United States Patent
Potze et al.

(10) Patent No.: US 9,771,978 B2
(45) Date of Patent: Sep. 26, 2017

(54) HYDRODYNAMIC BEARINGS

(71) Applicant: KONINKLIJKE PHILIPS N.V., Eindhoven (NL)

(72) Inventors: Willem Potze, Geldrop (NL); Anand Kumar Dokania, Best (NL); Gereon Vogtmeier, Aachen (DE); Peter Klaus Bachmann, Berlin-Kaulsdorf (DE); Christian Herbert Blome, Hamburg (DE); Michael Luebcke, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/119,246

(22) PCT Filed: May 27, 2015

(86) PCT No.: PCT/EP2015/061731
§ 371 (c)(1),
(2) Date: Aug. 16, 2016

(87) PCT Pub. No.: WO2015/185418
PCT Pub. Date: Dec. 10, 2015

(65) Prior Publication Data
US 2017/0102031 A1   Apr. 13, 2017

(30) Foreign Application Priority Data

Jun. 4, 2014 (EP) .................................... 14171080

(51) Int. Cl.
G11B 19/20 (2006.01)
F16C 17/02 (2006.01)
(Continued)

(52) U.S. Cl.
CPC ............ *F16C 33/106* (2013.01); *A61B 6/032* (2013.01); *F16C 17/026* (2013.01);
(Continued)

(58) Field of Classification Search
None
See application file for complete search history.

(56) References Cited

U.S. PATENT DOCUMENTS

| 3,453,159 A | 7/1969 | Vandersteen |
| 3,799,629 A | 3/1974 | Laing |

(Continued)

FOREIGN PATENT DOCUMENTS

| DE | 102008000554 A1 | 9/2009 |
| JP | 2002025483 A | 1/2002 |

(Continued)

OTHER PUBLICATIONS

Wang, Li-li et al "The numerical analysis of the radial sleeve bearing with combined surface slip" Tribology International, vol. 47, 2012, pp. 100-104.

(Continued)

*Primary Examiner* — Will J Klimowicz

(57) ABSTRACT

A self-acting, sealed hydrodynamic bearing includes a bearing shaft; a bearing bushing arranged to seal a length of the bearing shaft; a lubricant provided in the sealed length of the hydrodynamic bearing; and a bearing arrangement between the shaft and bushing. The bearing shaft and/or the bearing bushing are configured to be rotatable. The bearing arrangement includes a primary bearing surface disposed on the bearing bushing, arranged to face a secondary bearing surface disposed on the bearing shaft. The primary and/or secondary bearing surfaces includes first regions having a first fluid slip characteristic, and second regions having a second fluid slip characteristic substantially different to that (Continued)

of the first fluid slip characteristic. The second and first regions are in a same plane of a cross-section of the primary and/or secondary bearing surfaces, and are disposed in an interleaved pattern over the primary and/or secondary bearing surfaces.

14 Claims, 12 Drawing Sheets

(51) Int. Cl.
*F16C 33/10* (2006.01)
*F16C 17/10* (2006.01)
*F16C 43/02* (2006.01)
*A61B 6/03* (2006.01)
*H01J 35/10* (2006.01)
*G11B 33/14* (2006.01)

(52) U.S. Cl.
CPC .......... *F16C 17/105* (2013.01); *F16C 33/107* (2013.01); *F16C 43/02* (2013.01); *G11B 19/2036* (2013.01); *G11B 19/2045* (2013.01); *G11B 33/148* (2013.01); *H01J 35/101* (2013.01); *F16C 2202/54* (2013.01); *F16C 2316/10* (2013.01); *F16C 2370/12* (2013.01)

(56) References Cited

U.S. PATENT DOCUMENTS

| | | | | |
|---|---|---|---|---|
| 4,253,714 | A * | 3/1981 | Bhushan | ............... F16C 17/024 29/527.4 |
| 5,366,298 | A * | 11/1994 | Toshimitsu | ........... F16C 17/107 384/100 |
| 5,624,191 | A | 4/1997 | Fuchs | |
| 6,664,685 | B2 * | 12/2003 | Ameen | ................... F16C 17/10 310/45 |
| 2005/0175837 | A1 | 8/2005 | Massler | |
| 2006/0288579 | A1 | 12/2006 | Luo | |
| 2007/0283563 | A1 | 12/2007 | Lee | |
| 2009/0046960 | A1 | 2/2009 | Hibi | |
| 2012/0112587 | A1 * | 5/2012 | Kim | ...................... H02K 7/085 310/90 |

FOREIGN PATENT DOCUMENTS

JP      2002286026 A     10/2002
WO      2013046083 A1    4/2013

OTHER PUBLICATIONS

Fortier, Alicia et al "Numerical Analysis of a Journal Bearing With a Heterogeneous Slip/No-Slip Surface", The American Society of Mechanical Engineers, Journal of Tribology vol. 127 Issue 4.

* cited by examiner

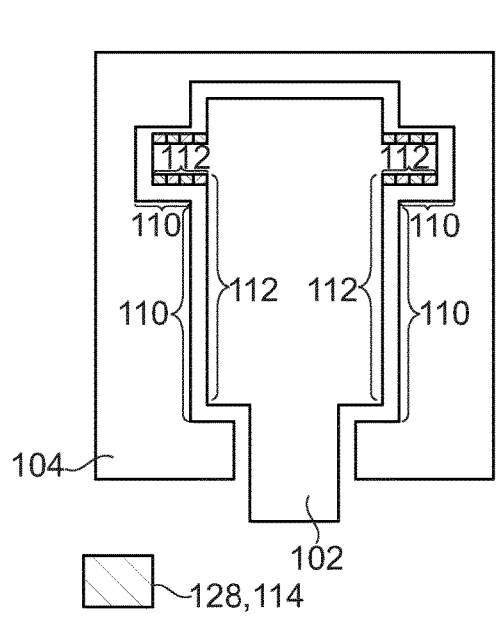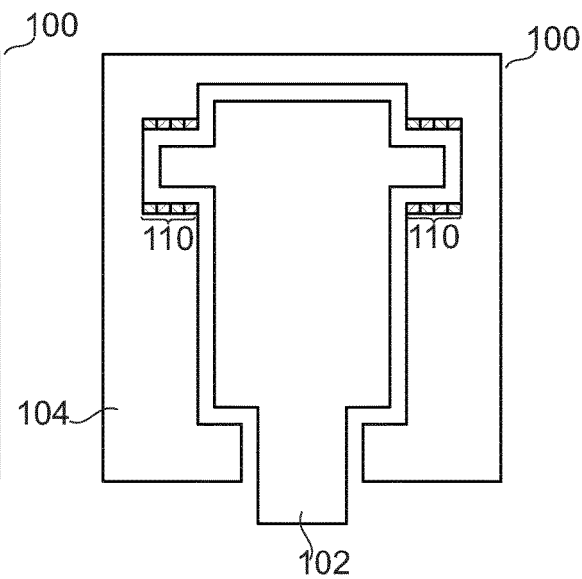
Fig. 5a      Fig. 5b
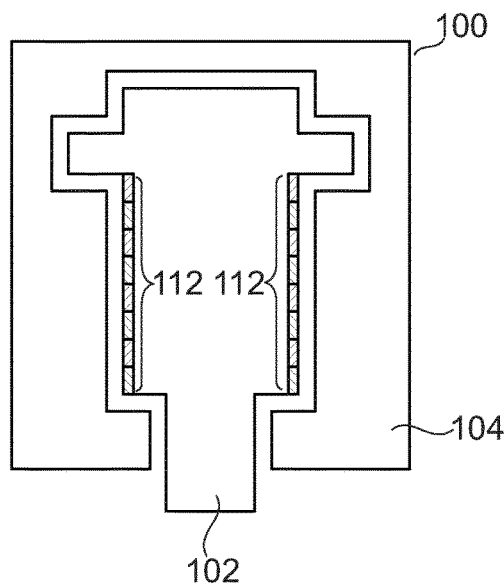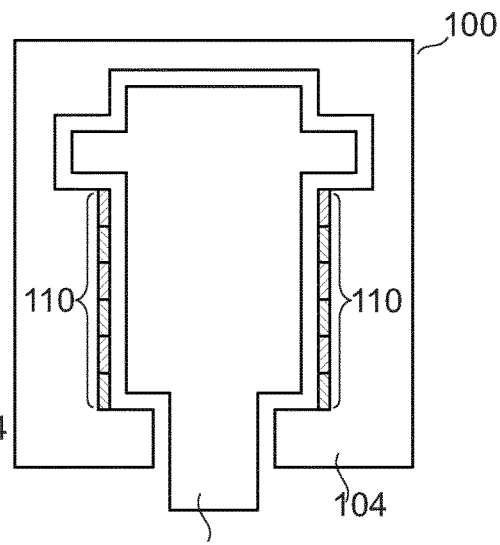
Fig. 5c      Fig. 5d

HYDRODYNAMIC BEARINGS

CROSS-REFERENCE TO PRIOR APPLICATIONS

This application is the U.S. National Phase application under 35 U.S.C. §371 of International Application No. PCT/EP2015/061731, filed on May 27, 2015, which claims the benefit of European Patent Application No. 14171080.6, filed on Jun. 4, 2014. These applications are hereby incorporated by reference herein.

FIELD OF THE INVENTION

The invention relates to a hydrodynamic bearing, an X-ray tube with a hydrodynamic bearing, an X-ray imaging system, a hard drive with a hydrodynamic bearing, and a method for manufacturing a hydrodynamic bearing.

BACKGROUND OF THE INVENTION

Hydrodynamic bearings are often used when a bearing must meet demanding performance conditions. In a hydrodynamic bearing, a gap between a rotor and a stator is formed. The gap contains a lubricant. The rotor is provided with a network of grooves. As the rotor rotates, fluid is forced into the network of grooves. A pressure is thereby generated in the fluid, which establishes a pumping action. In axial (thrust) bearings, the pumping action acts to raise the rotor in the bearing, thereby preventing contact between the rotor and the stator. In radial bearings, the pumping action acts to circulate fluid within the bearing.

WO 2013/046083 A1 discloses a hydrodynamic bearing for an X-ray tube, comprising a bearing shaft and a bearing bushing. The bearing bushing encloses the bearing shaft concentrically, and is rigidly connected to an anode disk and to a rotor. In addition, the bearing bushing is rotatably arranged on the bearing shaft. The bearing shaft and the bearing bushing are rotatable with respect to one another.

The properties of such hydrodynamic bearings can still be further optimized.

SUMMARY OF THE INVENTION

The object of the present invention is solved by the subject-matter of the independent claims, wherein further embodiments are incorporated into the dependent claims.

It should be noted that the following described aspects of the invention apply also to an X-ray tube containing a hydrodynamic bearing according to the invention, an X-ray system, to a hard drive containing a hydrodynamic bearing according to the invention, and to a method for manufacturing a hydrodynamic bearing.

According to the present invention, a hydrodynamic bearing is provided which comprises: a bearing shaft, a bearing bushing arranged to seal a length of the bearing shaft, and a lubricant provided in the sealed length of the hydrodynamic bearing. A bearing arrangement is provided between the bearing shaft and the bearing bushing, and the bearing shaft and/or the bearing bushing are configured to be rotatable.

The bearing arrangement comprises a primary bearing surface disposed on the bearing bushing, arranged to face a secondary bearing surface disposed on the bearing shaft.

The primary and/or secondary bearing surfaces comprise first regions having a first fluid slip characteristic, and second regions having a second fluid slip characteristic substantially different to that of the first fluid slip characteristic. The second and first regions are disposed in an interleaved pattern over the primary and/or secondary bearing surfaces.

Relative movement between the primary and secondary bearing surfaces caused by a rotation of the bearing shaft and/or the bearing bushing induces a pumping action in a body of lubricant in contact with the primary and secondary bearing surfaces, wherein the pumping action is induced by the difference in the fluid slip characteristics between portions of lubricant in contact with the interleaved pattern of the first and the second materials.

According to the invention, an X-ray tube is provided comprising a rotating anode, a cathode, and a hydrodynamic bearing as previously described. The rotating anode is supported on the bearing bushing of the hydrodynamic bearing. The anode disk provides a rotatable surface which is configured to generate X-rays as a result of electrons, emitted by the cathode, impinging on the rotatable disk.

According to the invention, an X-ray imaging system is provided. The system comprises: an X-ray tube as previously described, an X-ray detector, a support for receiving an object, and a processing device.

According to the invention, a hard drive is provided, comprising a supporting member, a hard disk comprising a central hub, and a hydrodynamic bearing as previously described. The central hub of the hard disk is rotatably supported on the supporting member by the hydrodynamic bearing.

According to the invention, a method for manufacturing a hydrodynamic bearing is provided. The method comprises the steps of:

(a) providing untreated bearing shaft and untreated bearing bushing parts;
(b) forming, on the surface of the untreated bearing shaft and untreated bearing bushing parts, a first region having a first fluid slip characteristic and a second region having a second fluid slip characteristic substantially different to that of the first fluid slip characteristic wherein the second and first regions are disposed in an interleaved pattern over the one or more bearing surfaces;
(c) assembling the bearing shaft and bearing bushing parts into a hydrodynamic bearing;
(d) adding a lubrication material into a gap between the bearing shaft and the bearing bushing;
(e) sealing the bearing.

The hydrodynamic bearing according to the invention increases the supportable load force, by allowing the removal of grooves in the bearing surfaces either partially, or entirely, across the bearing surfaces.

Therefore, a hydrodynamic bearing is provided wherein primary and/or secondary bearing surface comprise first regions having a first fluid slip characteristic, and second regions having a second fluid slip characteristic substantially different to that of the first fluid characteristic, wherein a pumping action caused by the difference in fluid slip characteristic replaces the pumping action caused by the grooves in prior art bearings.

In essence, as a fluid moves over bearing surfaces comprising such first and second regions disposed in an interleaved pattern, the fluid will experience a high degree of slip when in contact with one of the regions, and a low degree of slip when in contact with the other region. In other words, there is a difference in the fluid slip characteristics between the first region and the second region of the bearing surfaces. The difference in fluid slip characteristic causes a pressure variation in the fluid as it flows over the bearing surface. This pressure variation leads to a pumping action being induced in the fluid. The pumping action induced by the difference in the fluid slip characteristics is identical, or extremely similar, to the pumping action induced by groove arrangements.

This leads to substantial advantages. There is a significant improvement in load carrying ability of a hydrodynamic bearing according to the invention. Beneficially, a substantially planar coating can be applied to the bearing basis material, which can achieve a substantially similar pumping effect in a bearing according to the invention, as provided by grooves in prior art bearings. This leads to a significant improvement in the ease of manufacture of such bearings, since grooves of specific shapes and depths are difficult to manufacture at the required resolution.

In the following description, the term "bearing surface" refers to any region of a bearing which, in operation, is actively involved in providing a bearing action.

In the following description, the term "fluid slip characteristic" refers to the property of a solid material defining how it interacts with a fluid. A "low-slip" material substantially conforms to the assumption inherent in the "no-slip condition". This describes a material in which, when a fluid flows over its surface, the layer of molecules of the fluid directly in contact with the surface of the low-slip material does not move with respect to the rest of the fluid. In contrast, a material having the characteristic of "high-slip" is a material in which the no-slip condition is not valid. In other words, the layer of molecules of the liquid in immediate contact with the surface of the high-slip material will move, relative to the surface of the material.

One way of characterizing a fluid slip characteristic is using the metric of slip-velocity. For the same fluid conditions, a low-slip material will have a relatively low, or zero, slip velocity. Slip velocity may be viewed as a function of the wall shear stress. In contrast, the high-slip material will have a non-zero, and possibly significant slip-velocity. The specific slip-velocities depend on the combination of materials, fluid, flow, and pressure conditions present.

A related way of characterizing a fluid slip characteristic is with the metric of slip length. The slip length is the extrapolation distance inside a solid at which the fluid velocity relative to a wall vanishes. For a wall having no slip, the slip length is zero meters. In the following description, the term "interleaved pattern" refers to the result of depositing coating materials on a basis material alternately, and regularly, over a surface, thus forming a pattern. The pattern may be a herringbone, curved, spiral groove, or logarithmic spiral groove pattern, although other patterns may also be used.

The hydrodynamic bearing, the X-ray tube with a hydrodynamic bearing, the X-ray imaging system, the hard drive comprising a hydrodynamic bearing, and the method for manufacturing a hydrodynamic bearing according to the independent claims have similar and/or identical preferred embodiments, in particular, as defined in the dependent claims. The preferred embodiment of the invention can also be in any combination of the dependent claims with its respective independent claim.

These and other aspects of the present invention will become apparent from, and be elucidated with reference to, the embodiments described hereinafter.

BRIEF DESCRIPTION OF THE DRAWINGS

Exemplary embodiments to the invention will be described in the following with reference to the following drawings:

FIGS. 5A-5F show examples of the disposition of regions having different fluid slip characteristics, according to examples of the invention.

DETAILED DESCRIPTION OF EMBODIMENTS

Hydrodynamic bearings are used in demanding applications. Such applications require a high bearing speed, a high bearing load, and wide temperature tolerance. The simpler manufacture of such bearings is also desirable.

Figure 1:
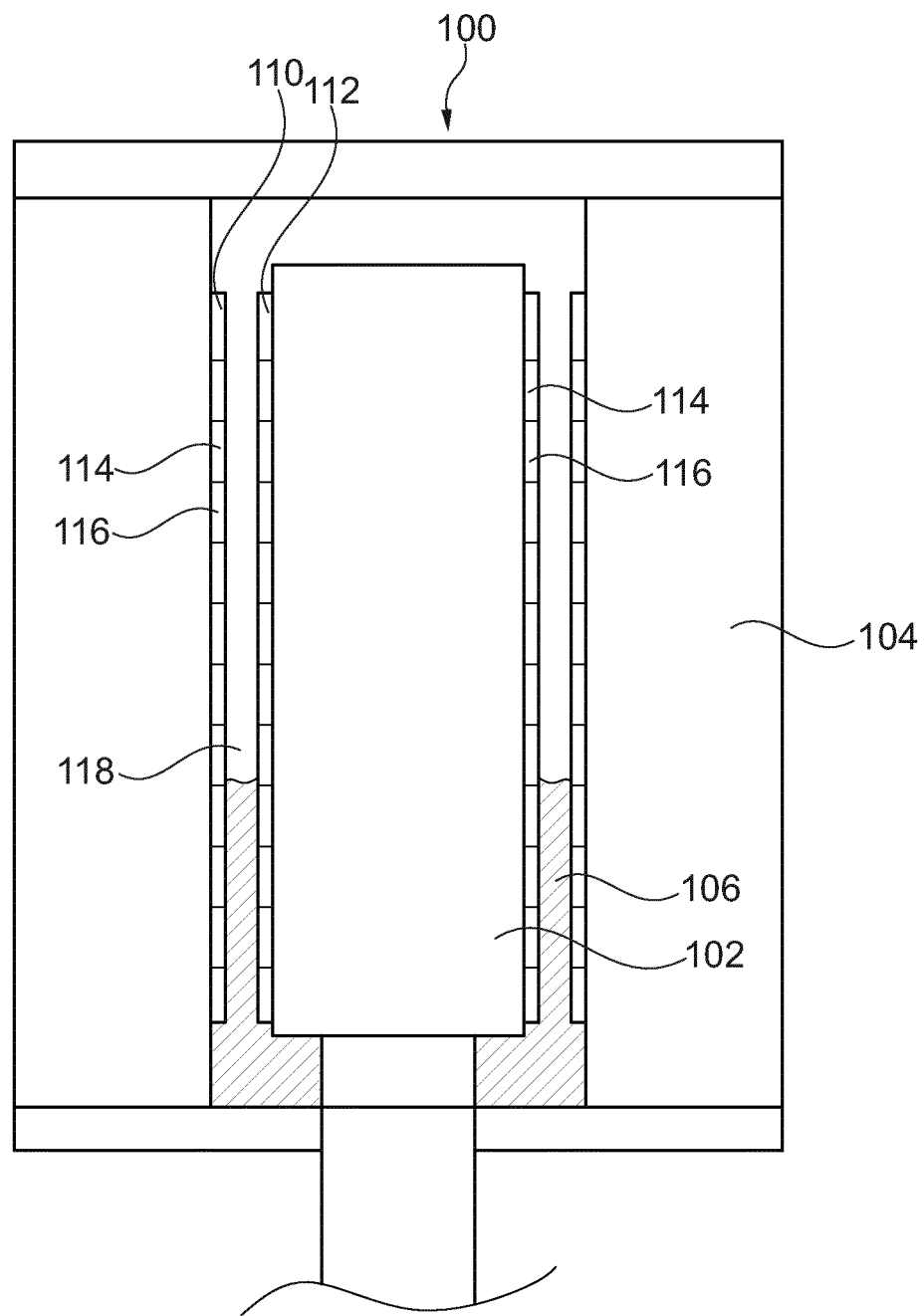
FIG. 1 shows a schematic view of a hydrodynamic bearing according to the invention.

FIG. 1 schematically shows a hydrodynamic bearing 100 according to the invention.

The hydrodynamic bearing 100 is provided which comprising: a bearing shaft 102, a bearing bushing 104 arranged to seal a length of the bearing shaft 102, and a lubricant 106 provided in the sealed length of the hydrodynamic bearing 100. A bearing arrangement is provided between the bearing shaft 102 and the bearing bushing 104.

The bearing shaft 102 and/or the bearing bushing 104 are configured to be rotatable.

The bearing arrangement comprises a primary bearing surface 110 disposed on the bearing bushing 104, arranged to face a secondary bearing surface 112 disposed on the bearing shaft 102.

The primary 110 and/or secondary 112 bearing surfaces comprise first regions 114 having a first fluid slip characteristic, and second regions 116 having a second fluid slip characteristic substantially different to that of the first fluid slip characteristic. The second and first regions are disposed in an interleaved pattern over the primary and/or secondary bearing surfaces.

Relative movement between the primary and secondary bearing surfaces caused by a rotation of the bearing shaft and/or the bearing bushing induces a pumping action in a body of lubricant in contact with the primary and secondary bearing surfaces, wherein the pumping action is induced by the difference in the fluid slip characteristics between portions of lubricant in contact with the interleaved pattern of the first and the second materials.

In an example, the bearing bushing is configured to rotate around a static bearing shaft. In this case, the bearing bushing is configured to support a load, such as a rotating anode disk of an X-ray source, or a hard-drive disk platen. In another embodiment, the bearing shaft is configured to rotate inside the bearing bushing. The bearing bushing is held stationary. The principles of operation discussed are also applicable in this case.

The primary and/or secondary bearing surfaces comprise first regions having a first fluid slip characteristic and second regions having a second fluid slip characteristic. When a section of the bearing shaft or the bearing bushing comprising such primary and/or secondary bearing surfaces rotates in a body of lubricant, a pumping action is established in the lubricant, because the first and the second fluid slip characteristics of the surfaces in contact with the lubricant are substantially different.

The surfaces of the bearing arrangements are, at least in part, substantially planar.

A pumping action can be established in the lubricant whilst causing a low, or zero shear stress. The frictional losses will, thus, be lower than those for a grooved bearing, because the first and second regions exert lubricant limited or no shear stress on the lubricant.

The delivered load force will be greater than for a conventional grooved bearing of the same dimensions. This advantageous behavior results because at least one of the bearing surfaces comprises a first region having a first fluid slip characteristic, and a second region having a second fluid slip characteristic substantially different to that of the first fluid slip characteristic. In other words, there is a substantial difference in fluid slip length between the surfaces of the first and second regions.

According to an embodiment of the invention, the first fluid slip characteristic is that of a high-slip material, and the second fluid slip characteristic is that of a low fluid slip material. When a surface comprising a low slip material moves in contact with a lubricant, a boundary layer of molecules of lubricant adheres to the wall of the moving surface and move at the same velocity as the moving surface. Therefore, the slip length of a low-slip material is negligible. When a lubricant is in contact with a moving surface comprising a region with a fluid slip characteristic having a high slip, the "no-slip condition" breaks down. Thus, there will be relative movement at the boundary between the outermost molecules of the lubricant, and the moving surface.

The second and first regions having first fluid slip characteristics and second fluid slip characteristics are disposed in an interleaved pattern over a bearing surface. This means that when a bearing surface having such an interleaved pattern moves relatively to a lubricant, portions of the lubricant will experience fluid slip. The portions of the lubricant will not experience fluid slip, the portions of fluid experiencing slip will therefore experience a flow resistance from the portions of the lubricant not experiencing fluid slip.

The implication of this is that regions of different pressure are formed in the lubricant, thus establishing a pumping action in the lubricant in contact with the bearing surface. This is analogous to the mechanism by which pumping is established in a bearing surface having grooves.

The absence of grooves moving in the fluid means that substantially zero shear stress is induced in the lubricant. Thus, the bearing is more energy-efficient. This means that for a fixed load tolerance, a smaller hydrodynamic bearing can be provided, according to the invention, than when compared with a conventional hydrodynamic bearing.

Another advantage is that the deposition of materials in the form of coatings in an interleaved pattern is easier than the provision of grooves in a repeating pattern. Therefore, another advantage experienced when using the invention is that the manufacture of the bearing shaft and/or the bearing bushing is easier.

The basis material of the bearing shaft and the bearing bushing is molybdenum, steel, tungsten, or any other suitable metal or plastic matched to the operating conditions of the bearing.

The lubricant 106 is provided as a liquid metal (metal eutectic) in high-performance applications, where heat transfer, heat tolerance, electrical conductivity, and thermal conductivity between the bearing shaft and the bearing bushing are required. Such liquid metals are known as a metal eutectic, which is a liquid alloy at room temperature, and remains a liquid at a temperature of up to 1300° C. The metal eutectic may comprise at least one of gallium, indium, and tin. For example, the metal eutectic is "galinstan", which comprises gallium, indium and tin.

In less demanding circumstances, other lubricants with suitable fluid performance for use in hydrodynamic bearing could be used without deviating from the teaching described herein. In particular, a hydrocarbon derivative such as oil, or ester oil, is used. Alternatively, silicone oil could be used.

According to an embodiment of the invention, the bearing gap is vacuum-sealed.

A range of materials can be applied to create the first region 114 and the second region 116 provided that a there is a difference in the fluid slip characteristic of the materials.

In the context of this application, a substantial difference in fluid slip characteristic is defined as a difference which leads to pumping behavior in the lubricant, as defined in the theoretical discussion which follows in this description.

According to an embodiment of the invention, a hydrodynamic bearing is provided wherein the first 114 and/or second 116 regions comprised on one or more of the bearing surfaces 110, 112 are arranged around the rotation axis of the hydrodynamic bearing in a spiral pattern, a herringbone pattern, or a curved pattern.

A bearing arrangement according to embodiments of the invention comprises an axial bearing, a radial bearing, or a combination of the two.

According to an embodiment of the invention, the hydrodynamic bearing comprises an axial bearing.

According to an embodiment of the invention, the hydrodynamic bearing comprises a radial bearing.

In the following section, the disposition of the interleaved pattern on regions of an axial (thrust bearing) will be considered. An axial hydrodynamic bearing, also known as a thrust bearing, is arranged to create a lift force on the bearing as the bearing shaft rotates relatively to the bearing bushing. This is caused by pressure exerted in a lubricant fluid, due to pumping in the lubricant caused by an interleaved pattern on the thrust bearing, most preferably a spiral pattern, which is located on a collar of the bearing shaft, or the bearing bushing, or both.

According to an embodiment of the invention, in the region of an axial (thrust) bearing, the bearing shaft comprises a collar, and the bearing bushing comprises a thrust disc to accommodate the collar. The collar is in the form of an annulus around the bearing shaft.

The collar and the thrust disc are, together, configured to form an axial bearing. The collar has first and second outer surfaces in the form of an annulus. The first and second surfaces are substantially perpendicular to the axis of the bearing shaft, connected by a third surface in the form of a cylindrical section. The third surface is substantially parallel to the axis of the bearing shaft.

In this embodiment, the thrust disc on the bearing bushing comprises the primary bearing surface, and the collar on the bearing shaft comprises the secondary bearing surface. In this embodiment, the combination of the primary bearing surface, the secondary bearing surface, and the interposed lubricant may be considered as a first bearing arrangement.

The bearing bushing comprises a fourth annular surface, facing the first outer surface of the collar. The bearing bushing comprises a fifth cylindrical sectional surface facing the third surface. The bearing bushing comprises a sixth annular surface facing the second surface.

Any one of, or all of, the interfaces between the first and fourth surfaces, the third and fifth surfaces, and the second and sixth surfaces is a bearing arrangement provided between the bearing shaft and the bearing bushing.

The first, second, and third surfaces as previously defined together, or individually, comprise a secondary bearing surface (on the bearing shaft).

The fourth, fifth, and sixth surfaces, as previously defined together, or individually, comprise a primary bearing surface (on the bearing bushing).

Any combination of the first to sixth surfaces, alone, or in combination, comprises first regions having a first fluid slip characteristic, and second regions having a second fluid slip characteristic substantially different to that of the second fluid slip characteristic, wherein the second and first regions are disposed in an interleaved pattern, preferably a spiral groove pattern, over the primary and secondary bearing surfaces.

According to an embodiment, the interleaved pattern is applied to the second surface. Thus, an axial thrust force against the sixth surface will be induced in the lubricant.

According to an embodiment, the interleaved pattern is applied, preferably as a spiral pattern, to the sixth surface. Thus, an axial thrust force against the second surface will be induced in the lubricant.

According to an embodiment, the interleaved pattern is applied to the first surface. Thus, an axial thrust force against the fourth surface will be induced in the lubricant. According to an embodiment, the interleaved pattern is applied to the fourth surface. Thus, an axial thrust force against the first surface will be induced in the lubricant.

According to an embodiment, the interleaved pattern is applied to the first and second surfaces in combination. Thus, an axial thrust force against the fourth and the sixth surfaces will be induced in the lubricant. Alternatively, or in combination, the interleaved pattern is applied to the fourth and sixth surfaces in combination. Thus, an axial thrust force against the first and the second surfaces will be induced in the lubricant.

According to a preferred embodiment, the interleaved pattern may be applied as a spiral pattern.

As a relative rotation is established between the bearing shaft 102 and the bearing bushing 104, the pumping action in the body of lubricant 106 established by the interleaved pattern of regions having a first fluid slip characteristic and a second fluid slip characteristic causes a pressure which lifts either the bearing bushing or the bearing shaft.

As the rotation speed increases, this force will be enough to lift either the bearing bushing or the bearing shaft into a position in the bearing where it is floating on a thin cushion of lubricant. Thus, the hydrodynamic bearing can support a load as it begins to turn. The rotation speed at which this occurs is influenced by the lift force generated by the interleaved pattern of first and second regions, the bearing geometry, the wetting interaction between the interleaved pattern and the lubricant 106, characteristics of the bearing component surfaces, the bearing's alignment, rotational speed, and the surface velocity.

Advantageously, according to the foregoing embodiment, the interleaved pattern on the surfaces is designed so that, for a preferred rotational operating velocity of the axial bearing, the thrust force generated at the preferred rotational velocity is sufficient to provide a force balance of a desired axial bearing load, such as an anode disk or a hard drive platen, and the bearing pumping action.

According to an embodiment, the interleaved pattern is applied, preferably as a herringbone pattern, to the third, the fifth, or the third and the fifth surfaces in combination.

Thus, a radial force against the fifth and third surfaces is generated, which serves to stabilize the collar end of the bearing shaft.

According to an embodiment of the invention, the hydrodynamic bearing comprises a radial bearing.

In the following section, the disposition of the interleaved pattern on regions of the radial bearing (journal bearing) will be considered. For the purposes of this section, it is clear that references to the interleaved pattern comprising a herringbone or curved pattern do not apply to embodiments of the invention concerning the axial bearing.

A radial hydrodynamic bearing, also known as a journal bearing, is arranged to create a radial force in a lubricant between the bearing shaft as the bearing bushing rotates. Thus, the combination of the journal (bearing shaft 102), the bearing bushing, and the interposed lubricant is a second bearing arrangement, wherein the bearing bushing is the primary bearing surface 110, and the journal (bearing shaft 102) is the secondary bearing surface.

When the second bearing arrangement is subject to a relative rotation, a force is exerted on the bearing surfaces. This is due to a pumping action induced in the lubricant, caused by an interleaved pattern which is located on the bearing shaft (journal), or the corresponding bushing, or both. Most preferably, the interleaved pattern is a herringbone or a curved pattern.

When the axis of the bearing shaft (journal) is perfectly aligned with respect to the axis of the bearing, the force generated in the lubricant by the pumping action at any arbitrary portion of the second bearing arrangement is balanced with the force on the opposite side of the journal. Therefore, in a situation where there the bearing shaft has no eccentricity with respect to the bearing bushing, the forces are balanced. As the journal begins to exhibit eccentricity, increasing pressure on the side of the journal extending closer to the bearing bushing functions to move the radial bearing back to a non-eccentric state.

In embodiments combining a radial, and an axial bearing, the radial bearing also functions to perform a pumping action which recirculates lubricant in the bearing gap back into the axial bearing.

The second bearing arrangement provided between the bearing bushing (primary bearing surface) and the bearing shaft (secondary bearing surface) comprises a seventh surface disposed on the bearing bushing, and an eighth surface disposed on the bearing shaft (journal).

According to an embodiment, the interleaved pattern is applied to the seventh surface. Thus, a radial thrust force against the journal will be induced in the lubricant. According to an embodiment, the interleaved pattern is applied to the eighth surface. Thus, a radial thrust force against the bearing bushing will be induced in the lubricant.

According to an embodiment, the interleaved pattern is applied to the seventh and the eighth surfaces. Thus, a radial thrust force will be induced in the lubricant.

According to preferred embodiments, the interleaved pattern on the surface of the radial bearing may be a herringbone, or curved pattern.

According to embodiments concerning a radial bearing, there is provided on the journal, or the bearing bushing, two separation grooves having no interleaved pattern, which divides the journal into three equal parts.

In the foregoing section, detailed embodiments of separate axial (thrust) and radial (journal) bearings were discussed. It is to be understood that in either case, the primary and/or secondary bearing surfaces comprise first regions having a first fluid slip characteristic, and second regions having a second fluid slip characteristic substantially different to that of the first fluid slip characteristic. The second and first regions are disposed in an interleaved pattern over the primary and/or secondary bearing surfaces.

This provides the advantageous behavior already described in respect of stand-alone axial bearings, and radial bearings.

According to an embodiment of the invention, the axial bearing (and its subordinate embodiments), and the radial bearing (and its subordinate embodiments) described previously is combined in the same hydrodynamic bearing to provide an additional synergetic effect.

According to an embodiment of the invention, the hydrodynamic bearing comprises an axial and a radial bearing, as previously described in any combination of the embodiments of axial and radial bearings described previously.

Figure 2:
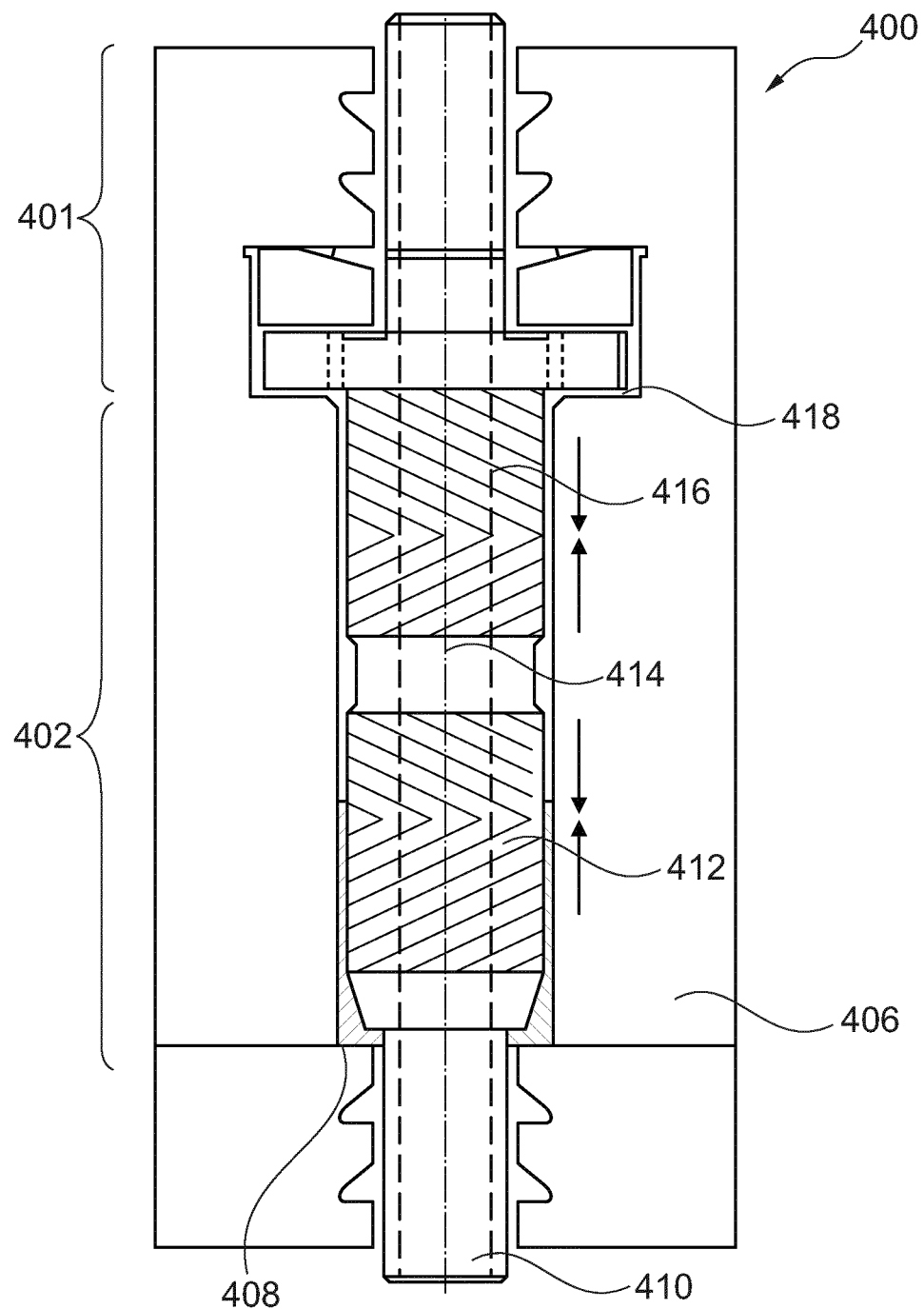
FIG. 2 shows a hydrodynamic bearing according to an example.

FIG. 2 illustrates such a combination of axial (thrust) and radial bearings in the same hydrodynamic bearing, according to an embodiment of the invention. In FIG. 2, a hydrodynamic bearing 400 is shown having an axial bearing 401 and a radial bearing 402. A lubricant 408 is present in the bearing gap. The bearings are formed between a bearing shaft 410, equivalent to the bearing shaft 102 in FIG. 1. The bearing shaft is contained within a bearing bushing 406, equivalent to the bearing bushing 104 in FIG. 1. In the embodiment of FIG. 2, the bearing shaft 410 is equivalent to the bearing shaft 102 of FIG. 1.

The bearing shaft 410 of the embodiment of FIG. 2 comprises two bearing arrangements. The first bearing arrangement, of the axial (thrust) bearing 401, is formed between a collar of the bearing shaft 410 and a thrust disc of the bearing bushing 406. The second bearing arrangement, of the radial bearing 402, is formed by a radial surface of the bearing shaft 410 and the bearing bushing 406.

The axial (thrust) bearing 401 comprises a primary bearing bushing arranged on the bearing shaft 410, and a secondary bearing surface arranged on the bearing bushing 418. The primary and secondary surfaces, or both, comprise first regions 114 having a first fluid slip characteristic, and second regions 116 having a second fluid slip characteristic substantially different to that of the first characteristic. The first and second regions are disposed in an interleaved pattern over the primary and/or secondary bearing surfaces.

The interleaved pattern takes the form of a spiral pattern or a log spiral pattern, or suitable variations evident to the skilled person, as discussed in connection with the embodiment of FIG. 1.

The alternative embodiments discussed above, defining first to sixth surfaces of an axial bearing, and variations of the arrangement of the interleaved pattern on the axial bearing, are also applicable in combination with the axial bearing section 401 of the embodiment of FIG. 2.

Illustrated in FIG. 2 is a radial bearing 402 in which another primary bearing surface is located on a radial section of the bearing shaft 410, and another secondary bearing surface 406 is located on a radial section of the bearing bushing 406. In the embodiment illustrated in FIG. 2, the primary bearing surface is divided into a first primary bearing surface 412, and a second primary bearing surface 412, by a separation gap 414. The first primary bearing surface and the second primary bearing surface comprise an interleaved pattern comprising first and second regions, wherein the first region has a fluid slip characteristic substantially different to that of the first fluid slip characteristic.

The separation gap decouples the first primary bearing surface and the second primary bearing surface. Then the first primary bearing surface and the second primary bearing surface act as two independent radial bearings. The separation gap means that there will be no interaction between the first and the second bearing surfaces. This is advantageous for stability reasons.

In an alternative embodiment, a radial section 410 of the bearing shaft has no separation gap. In other words, it has a unitary primary bearing surface having an interleaved pattern.

The first primary bearing surface 412, and a second primary bearing surface 412 is a herringbone, asymmetrical herringbone, or curved pattern.

The operation of the hydrodynamic bearing 400 discussed previously will now be described. When in a stationary position, the bearing shaft is settled, and in contact with the bearing bushing. The lubricant will be settled in a portion of the bearing gap 118, shown FIG. 1. As a rotational force is applied to the bearing shaft 410, a pumping action will be induced in the lubricant by the first and second regions disposed in an interleaved pattern over the bearing surfaces. The force generated between the radial section of the bearing shaft and bearing bushing stabilizes the shaft. In the axial bearing, another pumping action functions to force either the collar of the bearing shaft, or the thrust disc of the bearing bushing, away from each other (dependent on the disposition of the primary and secondary bearing surfaces in accordance with embodiments discussed above). Thus, the shaft floats on a cushion of lubricant.

According to an embodiment of the invention, the difference in the fluid slip characteristic between the first region and the second region is at least 25%. According to an alternative embodiment, the difference in the fluid slip characteristic between the first region and the second region is at least 15%. According to an alternative embodiment, the difference in the fluid slip characteristic between the first region and the second region is at least 50%. According to an embodiment of the invention, the interleaved pattern disposed over the primary and/or secondary bearing surfaces is in a spiral pattern.

According to an embodiment of the invention, the hydrodynamic bearing comprises axial bearings and/or radial bearings as previously described. The lubricant is maintained in the bearing system by the self—sealing effect of the generated pumping action caused by the relative sliding motion of the bearing parts and the coatings with different slip properties.

Figure 3A:
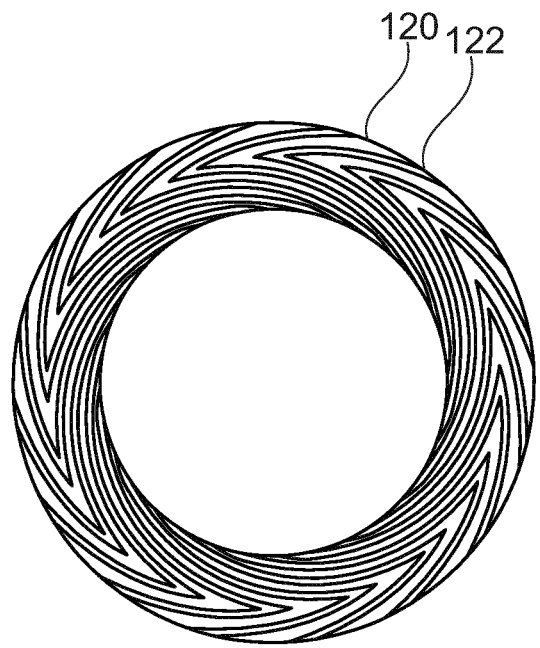
FIG. 3 shows interleaved patterns according to examples of the invention.

FIG. 3A illustrates a spiral pattern suitable for use in an axial hydrodynamic bearing. The dark area 120 represents a region having a first fluid slip characteristic, and region 122 denotes a region of the axial bearing having a second fluid slip characteristic. These fluid slip characteristics are substantially different to each other.

The bearing bushing or bearing shaft of an axial bearing may use alternative patterns, provided that when relative movement occurs in the presence of a lubricant, an axial thrust force is developed between the bearing bushing and the bearing shaft. For example, a logarithmic spiral pattern can be applied.

As discussed above, it is also known to provide bearing arrangements as radial bearings. Radial bearings are provided in a herringbone or curved groove pattern around the outside of a bearing shaft 102 or the inside of a bearing bushing 104, or both. In this case, the interleaved pattern is a herringbone or curved pattern disposed on the primary bearing surface, or the secondary bearing surface, or both.

Figure 3B:
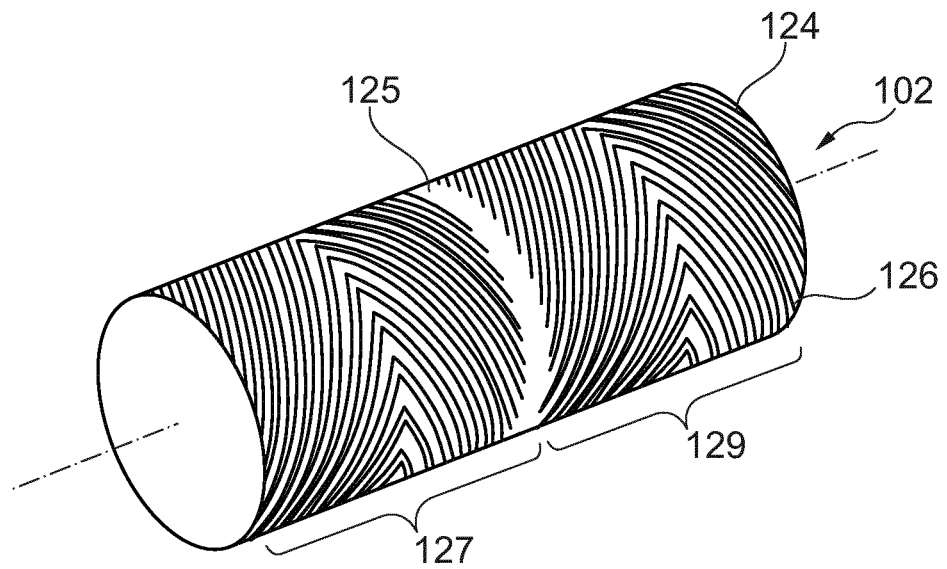

FIG. 3B shows an isometric view of a bearing shaft 102 comprising a region 124 which is a first region having a first fluid slip characteristic and a second region 126 having a second fluid slip characteristic substantially different to that of the first fluid slip characteristic. The radial bearing could be provided on the inside of the bearing bushing 104.

In operation, the rotation of the bearing shaft or the bearing bushing induces a pumping action in a body of lubricant in contact with the radial bearing according to the technical principle stated previously.

Therefore, according to an embodiment of the invention, wherein the first region (116) is formed from a substantially planar coating of a first material, and the second region (116) is formed from a substantially planar coating of a second material.

The first and second regions can be coated onto the bearing bushing or the bearing shaft by processes known to those skilled in the art such as plasma vapour deposition or chemical vapour deposition. Such processes can allow an accurate deposition of the interleaved pattern, which results in a simple manufacturing process.

According to an embodiment of the invention, a hydrodynamic bearing 100 is provided wherein the second material having a second fluid slip characteristic is the basis material of the bearing shaft 102 and/or the bearing bushing 104.

As discussed previously, examples of the basis material of a high performance hydrodynamic bearing are metals, such as molybdenum or tungsten. The fluid slip characteristic of molybdenum may be adjusted through processes such as chemical etching, blasting with a carbide dust, or a heat treatment.

In an embodiment, the first material is deposited in an interleaved pattern, leaving exposed the second region as basis material. The first material is not wetted by a liquid metal lubricant. The bare basis material (a metal such as molybdenum) is wetted by a liquid metal lubricant.

Therefore, according to this embodiment, only one coating would need to be applied to the bearing shaft, the bearing bushing, or both. The fluid slip characteristic substantially different to that of the first fluid slip characteristic would result from the action of the lubricant as it passed over the basis material of the bearing shaft 102 and/or the bearing bushing 104.

According to an embodiment of the invention, a hydrodynamic bearing 100 is provided wherein the thickness of the first region 114 is less than 5 microns. According to a preferred embodiment, a hydrodynamic bearing 100 is provided wherein the thickness of the first region is less than 2 microns. According to another embodiment, a hydrodynamic bearing is provided wherein the thickness of the first region is less than 1 micron.

Figure 4:
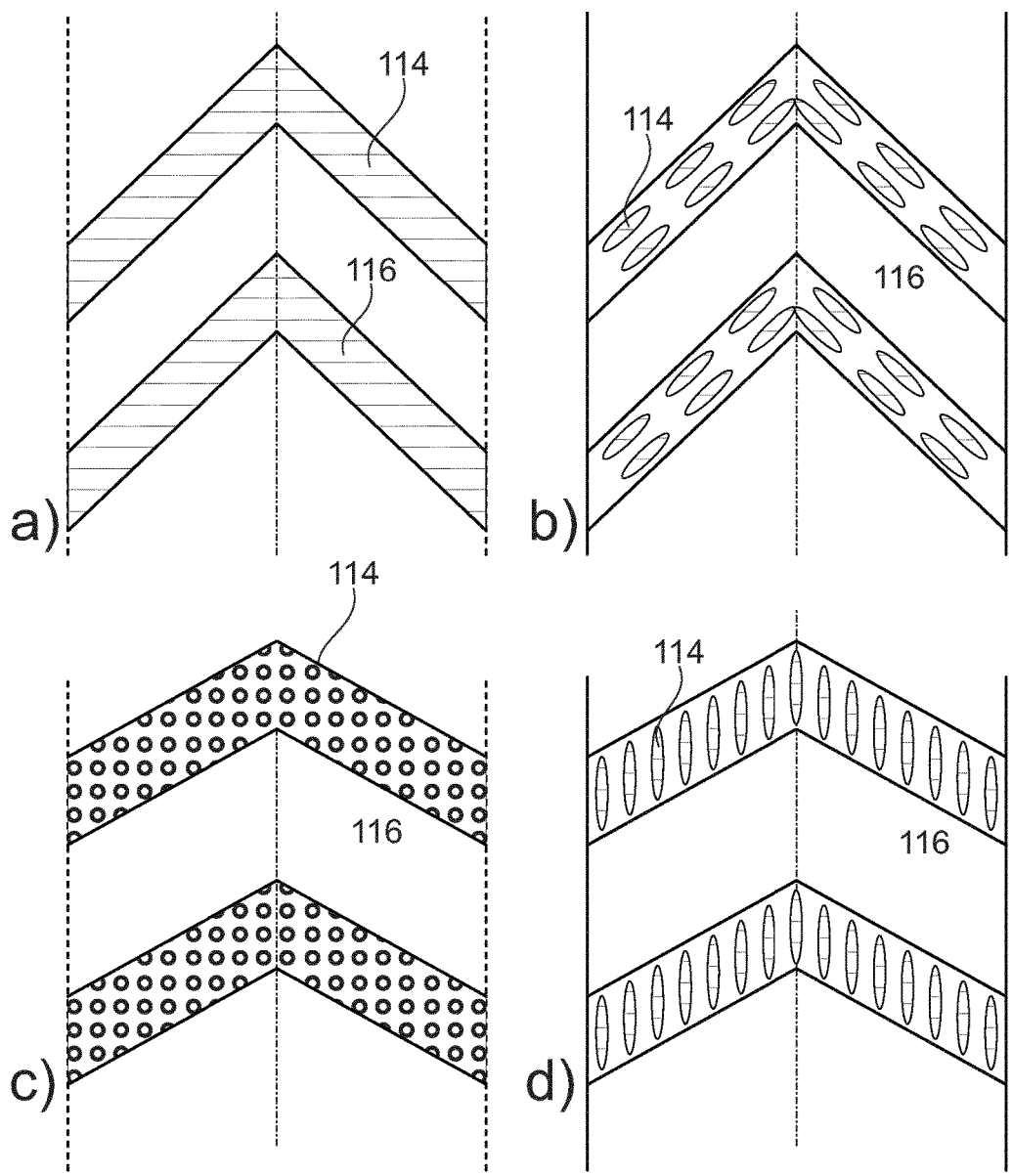
FIGS. 4A-4D show details of bearing coatings according to examples of the invention.

FIG. 4 shows some alternative embodiments of coating techniques of the second and first regions disposed in an interleaved pattern over the primary and/or secondary bearing surfaces.

In FIG. 4A there is shown a preferred embodiment of a coating technique, comprising a herringbone pattern in which the first region 114 is provided as a unitary coating of material in a herringbone pattern. The second region 116 is provided as another unitary area of material comprising either a coating having a second fluid slip characteristic, or the basis material of the bearing bushing or the bearing shaft.

FIG. 4B shows an alternative embodiment of a coating technique comprising an interleaved pattern in which the first region 114 comprises a distribution of lozenge-shaped areas deposited in a herringbone pattern, and a second region 116 formed either of a second coating in a herringbone pattern, or as the basis material of the shaft.

In FIG. 4C, an alternative embodiment of a coating technique is shown wherein the first region 114 is provided as a series of first regions having a first fluid slip characteristic deposited on the bearing shaft or the bearing bushing in a dot formation conforming to a herringbone pattern, alternating with a second coating and/or the basis material of the bearing shaft or the bearing bushing.

In FIG. 4D, an alternative embodiment of a coating technique is shown where the first region is provided as lozenge-shaped regions extending in the direction of the herringbone pattern, and the second region is provided either as a second coating, or as the basis material of the shaft or the bearing bushing.

Other patterns, such as a spiral groove pattern or a curved pattern can be provided according to the principles illustrated in FIG. 4. The technical operation of the interleaved pattern which induces a pumping action in a lubricant is still preserved in these coating embodiments. The first regions 114 having a first fluid slip characteristic will still operate to induce the pumping action.

FIGS. 5A to 5F illustrate alternative embodiments of the distribution of the primary bearing surface and the secondary bearing surface. The drawings are cross-sections of the bearing arrangement through the central axis of the bearing. Therefore, only the location of coatings on the bearing parts is represented.

In FIGS. 5A to 5F, a first region having a first fluid slip characteristic is illustrated with hatching 128, and the second region having a second fluid slip characteristic is illustrated with hatching 130.

FIG. 5A shows a hydrodynamic bearing 100, a bearing bushing 104, and a bearing shaft 102. Disposed on the bearing bushing 104 is a primary bearing surface 110. On the bearing bushing is a secondary bearing surface 112.

FIG. 5A shows an preferred embodiment of the axial bearing coating, where the secondary bearing surface 112 having first regions 114 and second regions 116 having fluid slip characteristics substantially different to each other is disposed on the collar of the thrust bearing formed on the bearing shaft.

FIG. 5B shows an alternative embodiment of the axial bearing. In this case, the thrust bearing is formed by a spiral pattern of first and second regions arranged on the bearing bushing so as to face the collar of the bearing shaft 102.

FIG. 5C shows a radial bearing according to an embodiment of the invention. In FIG. 5C, the secondary bearing surface 112 is disposed around the bearing shaft. The first and second regions are disposed in a herringbone, curved, or equivalent pattern around the bearing shaft.

FIG. 5D shows another radial bearing according to an alternative embodiment of the invention. In FIG. 5D, the primary bearing surface 110 is disposed to form a radial bearing on the surface of the bearing bushing. Thus, the first regions and the second regions are disposed in an interleaved pattern, such as a herringbone pattern over the inside of the bearing bushing.

Figures 5E, 5F:
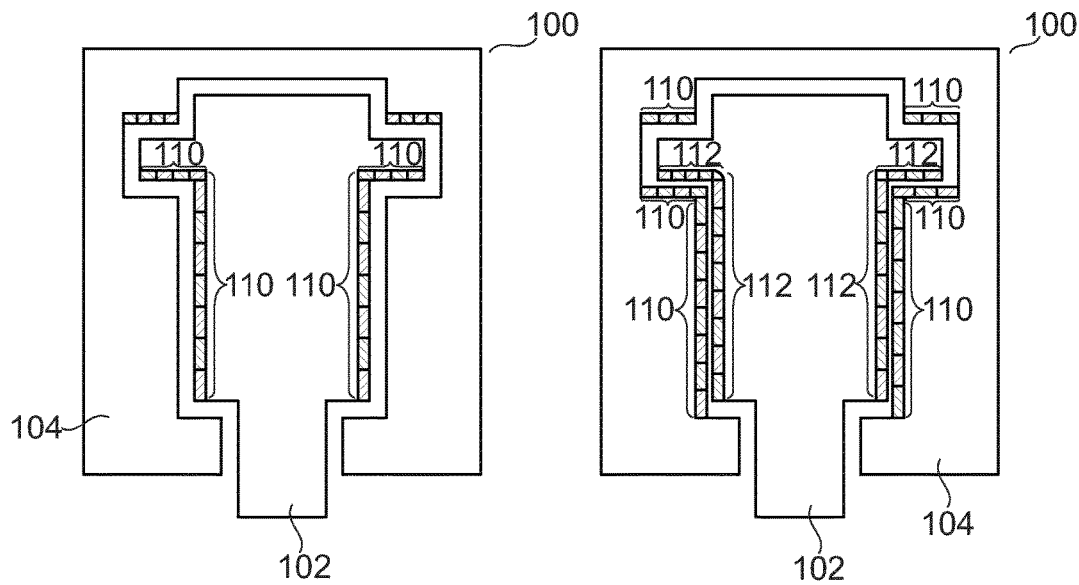

FIG. 5E illustrates another alternative embodiment of the invention. In FIG. 5E, the primary bearing surface 110 forms both a thrust bearing and a radial bearing on the surface of the bearing shaft 102.

FIG. 5F shows an alternative embodiment of the invention. In this embodiment, primary bearing surfaces 110 are disposed on the bearing bushing 104 and secondary bearing surfaces 112 are disposed on the bearing shaft 102. In this embodiment, there are thrust and radial bearings present on both the bearing shaft and the bearing bushing.

According to an embodiment of the invention, a hydrodynamic bearing 100 is provided wherein the first 114 and/or second 116 regions of the interleaved pattern are provided in first 127 and/or second 129 sections of the first 110 and/or second 112 bearing surfaces, wherein the first and/or second regions are divided by a separation region 125.

With reference to FIG. 3B, it can be seen that two interleaved patterns, in the form of herringbone patterns, are provided in first 127 and second 129 sections of the radial bearing surface illustrated. A wider separation region between the two herringbone patterns is also provided 125. The pumping action provided by the radial bearing is improved by the presence of the separation region.

Figure 6:
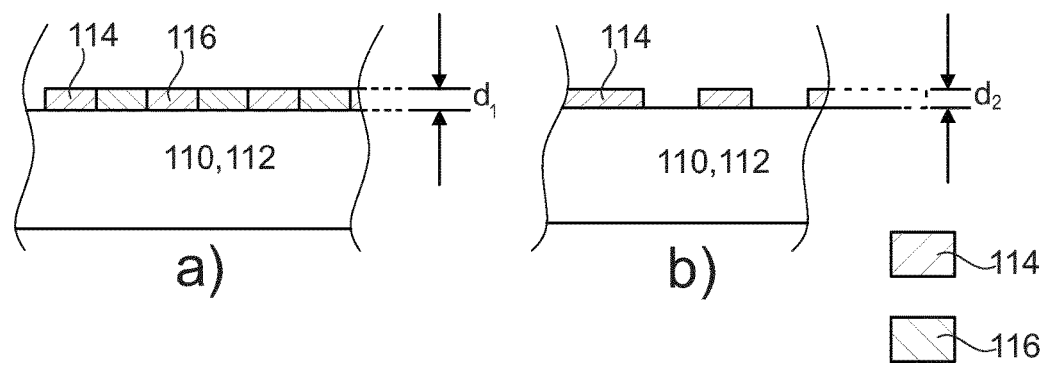
FIGS. 6A and 6B show examples of a bearing surface according to examples.

FIG. 6A shows a cross-section of a bearing surface according to an embodiment of the invention. A bearing surface coated in an interleaved pattern with first regions 114 having a first fluid slip characteristic and second regions 116 having a second fluid slip characteristic is shown. In FIG. 6A, the dimension $d_1$ represents the thickness of the first, the second, and/or both coatings. In an embodiment, $d_1$ is less than 5 µm. In an alternative embodiment, $d_1$ is less than 2 µm. In another embodiment, $d_1$ is less than 1 µm.

FIG. 6B shows a situation where only a first region 114 is deposited on a bearing surface, and the second material having a second fluid slip characteristic is the basis material of the bearing shaft 102 and/or the bearing bushing 104. As can be seen, the coating thickness is illustrated by dimension $d_2$. In an embodiment, $d_2$ is lower than 5 µm. In a further embodiment, $d_2$ is lower than 2 µm. Finally, in an embodiment, $d_2$ is lower than 1 µm.

In FIG. 6A, the first region 114 and the second region 116 have a substantially planar surface. Therefore, the bearing surface 110 or 112 when coated in such a manner will exert negligible shear stress into a lubricant 106. In FIG. 6B, the distance $d_2$ by which the first region 114 projects away from the bearing surface 110, 112 is so small that negligible shear stress is experienced in the lubricant 106.

According to an embodiment of the invention, a hydrodynamic bearing 100 is provided wherein the bearing bushing 104 and the bearing shaft 102 are provided as a conical bearing 200, or as a spherical bearing 202.

Figure 7:
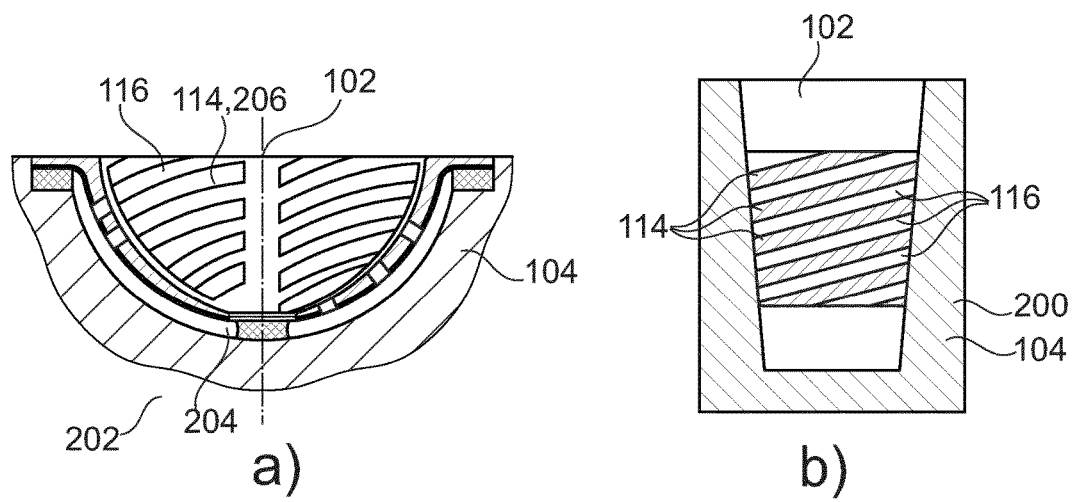
FIGS. 7A and 7B show alternative types of bearing according to examples.

FIG. 7A illustrates a spherical bearing 202 with a bearing bushing 104 and a bearing shaft 102. The bearing shaft is provided in a substantially hemispherical form. The bearing bushing 104 is a hemispherical socket. The bearing bushing and bearing shaft are sealably connected. The gap 204 receives a lubricant 106. An interleaved pattern 206 is provided around the surface of the hemispherical bearing shaft. This interleaved pattern can also be provided on the surface of the hemispherical socket. As has previously been the case, the interleaved pattern comprises first regions 114 having a first fluid slip characteristic and second regions 116 having a second fluid slip characteristic. According to the principle of operation outlined previously, a relative movement between the surfaces caused by a rotation of the bearing shaft and/or the bearing bushing induces a pumping action in a body of lubricant in contact with the primary and secondary bearing surfaces, wherein the pumping action is induced by the difference in the fluid slip characteristics between portions of lubricant in contact with the interleaved pattern of the first and second materials.

FIG. 7B shows a conical bearing 200 comprising a bearing shaft 102 and a bearing bushing 104. The bearing shaft 102 is in the form of a cone, and the bearing bushing is in the form of a conical socket. The bearing bushing and bearing shaft are sealably connected. Illustrated is a bearing shaft 102 in a conical form with an interleaved pattern of first regions 114 having a first fluid slip characteristic and second regions 116 having a second fluid slip characteristic substantially different to that of the first fluid slip characteristic. As stated above, relative movement between the primary and secondary bearing surfaces caused by a rotation of the bearing shaft and/or the bearing bushing induces a pumping action in the body of the lubricant in contact with the primary and secondary bearing surfaces. The pumping action is induced by the difference in the fluid slip characteristics between portions of lubricant in contact with the interleaved pattern of the first and second materials.

According to an embodiment of the invention, a hydrodynamic bearing is provided wherein the first region 114 is coated with an ultra-nano-crystalline diamond film.

Ultra-nano-crystalline diamond is one of the smoothest diamond films available with a surface having a root mean square roughness of lower than 12 nm. Therefore, is has a very high fluid slip characteristic.

According to an embodiment of the invention, a hydrodynamic bearing 100 is provided wherein the first and/or second region comprises a coating of any material selected from the group of: molybdenum disulphide, amorphous carbon, tetrahedrally coordinated amorphous carbon, polycrystalline diamond, and tungsten disulphide.

These materials have different fluid slip characteristics. Their application to the second and first regions in an interleaved pattern over the primary and/or secondary bearing surfaces enables the differential in fluid slip characteristic to be provided.

According to an embodiment of the invention, a hydrodynamic bearing 100 is provided wherein the first 114 and/or second 116 primary bearing surfaces further comprises a first grooved portion 170 having a plurality of ridges 172 and grooves 174, wherein the coating of the first region is applied in the grooves of the first grooved portion.

Figure 8:
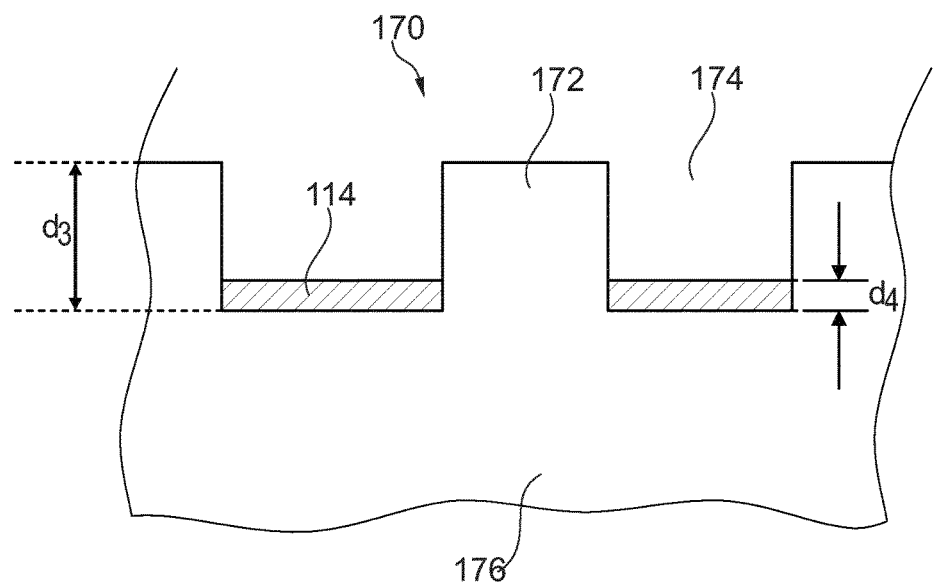
FIG. 8 shows a grooved bearing surface according to examples.

FIG. 8 illustrates this embodiment of the invention. What is shown is a section of basis material 176 which is comprised either in the first or the second primary bearing surface. Provided in the bearing surface is a plurality of grooves which are produced using laser etching, chemical etching, or other methods known to the skilled in the art. The coating of the first region is applied in the grooves 174.

As indicated by the distance arrows $d_3$ and $d_4$, the depth of the grooves 174 is much greater than the height of the coating of the first region 114. As discussed previously, the thickness of the coating of the first region $d_4$ is lower than 10 µm, lower than 5 µm or lower than 2 µm. In comparison, the depth of the groove $d_3$ is greater than 15 µm.

Therefore, it can be seen that there is a significant distinction between the thickness of the coating applied to the first region 114, and the thickness of the grooves.

The combination of the grooves, and the slip coating in the grooves, combines the effect of the grooves and that of the slip coating. Therefore, there is observed an improvement of bearing performance manifested by a greater load carrying capacity, at the cost of lower frictional losses.

In the foregoing description, it has been stated that a basic idea of the invention is to provide bearing surfaces comprising first regions 114 having a first fluid slip characteristic, and second regions 116 having a second fluid slip characteristic substantially different to that of the first fluid slip characteristic. The second and first regions are disposed in an interleaved pattern over the primary and/or secondary bearing surfaces. Relative movement between the primary and secondary bearing surfaces caused by a rotation of the bearing shaft and/or the bearing bushing induces a pumping action in a body of lubricant in contact with the primary and secondary bearing surfaces, wherein the pumping action is induced by the difference in the fluid slip characteristics, between portions of lubricant in contact with the interleaved pattern of the first and the second materials.

In essence, therefore, a differential between the fluid slip characteristics of different interleaves coatings can establish in a fluid a pumping action. This pumping action is analogous to the pumping established in a fluid by grooves in contact with the fluid. This enables the substitution of grooves in a hydrodynamic bearing with a region of interleaved coatings having different fluid slip characteristics.

This principle will be further expounded upon below.

Figure 9A:
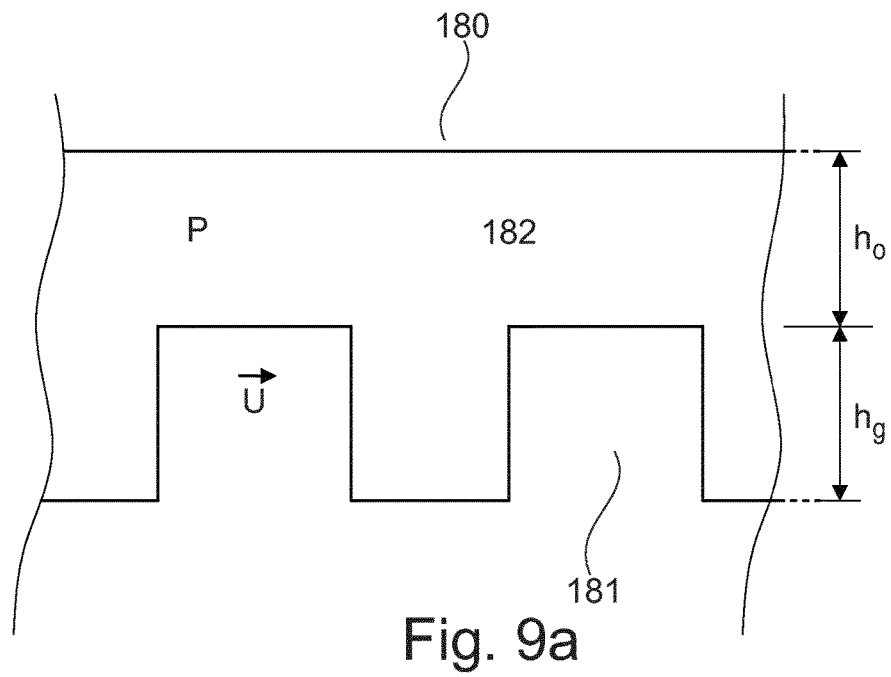
FIGS. 9A and 9B show exemplary comparisons of grooved and non-grooved bearing surfaces.

FIG. 9A shows an upper 181 and lower bearing surface 180 enclosing a lubricating fluid. The lower bearing surface comprises grooves, and is configured to move relatively to the upper bearing surface. Such a surface is typically found in a hydrodynamic (self-acting) bearing. A self-acting bearing comprises grooves disposed in a spiral pattern (axial or thrust bearing), and/or a radial bearing comprising grooves disposed in a herringbone pattern. The assumptions made in the following analysis are valid for these cases, and other variations that will be apparent to the person skilled in the art.

In the illustrated situation, the pressure p of the fluid in a conventional hydrodynamic bearing is characterized by the Reynolds equation (1):

$$\vec{\nabla} \cdot \left( \frac{h^3}{12\mu} \vec{\nabla} p + \frac{h}{2} \vec{U} \right) = 0 \tag{1}$$

The lower bearing surface 180 comprises grooves having a height $h_g$. The distance between the top of the grooves and the upper bearing surface is $h_0$. The bearing gap 182 contains a fluid, such as a lubricant, having a pressure p. The bearing surface moves, relatively to the upper bearing surface, with velocity $\vec{U}$. The distance between the top of the groove and the bottom of the groove, in other words the groove depth is $h_g$.

Therefore, the distance between the bearing surfaces is different to that on the location of a groove. Hence, if the distance between the bearing surfaces on the location of a ridge is $h_0$, then that at the location of the bottom of a groove is $h_0+h_g$. As is known to those skilled in the art, if the variation between ridges and grooves in the region between the upper 180 and lower 181 bearing surfaces is as shown in FIG. 9A, a pumping action is generated in the lubricant such that the bearing is self-acting.

The modified Reynolds equation for determining the pressure p in the lubricant of a bearing coated with a material having a high slip is as stated by Salant & Fortier, in "Tribology Transactions", 47, pp. 328-334, 2004:

$$\vec{\nabla} \cdot \left\{ \frac{-h^3}{12\mu} \left[ 1 + \frac{3\alpha\mu}{h+\alpha\mu} \right] \vec{\nabla} p + \frac{h}{2} \left[ 1 + \frac{\alpha\mu}{h+\alpha\mu} \right] \vec{U} - \frac{\tau_c}{2\mu} \frac{\alpha h^2}{h+\alpha\mu} \{ \pm \vec{e}_U \pm \vec{e}_{\perp U} \} \right\} = 0 \tag{2}$$

In addition to the previous parameters, α is the slip coefficient of a bearing material, and $\tau_c$ is the critical shear stress in the fluid. It is observed that by setting $\tau_c=0$, the equation quoted above reduces to:

$$\vec{\nabla} \cdot \left\{ \frac{-h^3}{12\mu} \left[ 1 + \frac{3\alpha\mu}{h+\alpha\mu} \right] \vec{\nabla} p + \frac{h}{2} \left[ 1 + \frac{\alpha\mu}{h+\alpha\mu} \right] \vec{U} \right\} = 0 \tag{3}$$

Comparison of equation (3) with equation (1) reveals that in a bearing containing surfaces coated with a material exhibiting "slip" style behavior, by setting the critical shear stress to zero, a similar expression to the Reynolds equation (1) is yielded. In the case of a no-slip surface, α=0, the square-bracketed terms in (3) reduce to unity, and the original Reynolds equation is reached. For completeness, in a surface having slip, α=1.

Figure 9B:
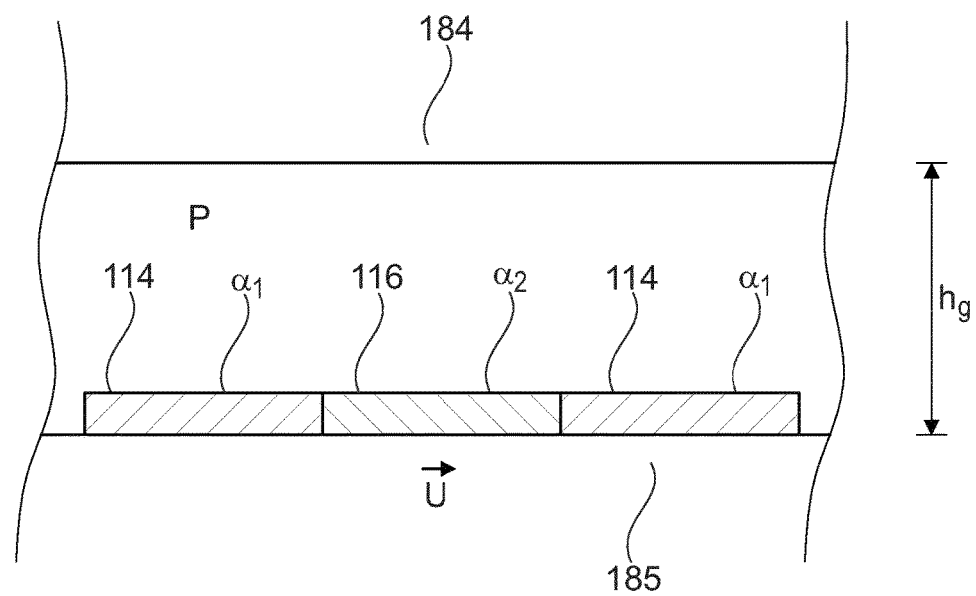

FIG. 9B illustrates a bearing surface according to the present invention. There is a lower 185 and upper 184 bearing surface enclosing a bearing gap, filled with a lubricant (fluid). In other words, the lower bearing surface 185 corresponds to a primary bearing surface 110, and the upper bearing surface 184 corresponds to a secondary bearing surface 112. The distance between the top of the groove and the bottom of the groove, in other words the grove depth, is $h_g$. The lubricant fluid is held at pressure p. The lower bearing surface 185 moves relative to the upper bearing surface with velocity $\vec{U}$.

Fluid slip results from a fluid-solid interaction. Aspects of the fluid, the surface, and the flow conditions may influence the slip experienced. In terms of the fluid, factors such as the viscosity, yield-stress, and density may play a role. In terms of the surface, the material and composition of the surface, and the deposition of different materials, may play a role. Materials having a different wettability, or roughness, may play a role.

The slip length is a measure of the magnitude of the fluid slip present at a fluid-solid interface. It is defined as the extrapolation distance inside the solid at which the fluid velocity relative to the interface vanishes. Reported values of slip lengths range between a few micrometers, and a few nanometers.

Disposed on the lower bearing surface 185 are first regions having a first fluid slip characteristic $\alpha_1$, and second regions having a second fluid slip characteristic $\alpha_2$.

In embodiments of the invention, the fluid slip characteristic of the first and second regions is substantially different, although for the purposes of this analysis $\alpha_1$ and $\alpha_2$ assume any value. As seen in FIG. 9B, the first regions and the second regions are disposed in an interleaved pattern over the lower bearing surface 185 (primary bearing surface 110).

In the case that a bearing surface contains a pattern wherein the first regions 114 comprise a material having "slip", and the second regions 116 comprise a material having "no-slip" surfaces in contact with the lubricant regions. In this case, the following conditions are present, as examples:

$$\alpha_1=1; \alpha_2=0 \quad (4)$$

In this case, as the length of the bearing in FIG. 9B is traversed by a lubricant droplet or portion, the coatings of the first and second regions in contact with the droplet or portion will alternate, presenting different slip characteristics to portions of lubricant in contact with that part of the surface. In other words, the term in (3):

$$h^3\left[1 + \frac{3\alpha\mu}{h + \alpha\mu}\right] \quad (5)$$

Changes alternately from $h^3$ to $$h^3\left[1 + \frac{3\alpha\mu}{h + \alpha\mu}\right] > h^3,$$

and back, as the bearing surface 185 is traversed. Likewise, the term in (3):

$$h\left[1 + \frac{\alpha\mu}{h + \alpha\mu}\right] \quad (6)$$

Changes from h to $$h\left[1 + \frac{\alpha\mu}{h + \alpha\mu}\right] > h$$

and back as the bearing surface 185 is traversed.

It will be noted that as the traversal across the interleaved pattern of the first and second regions progresses, an alternation of the terms of the characteristic equation (3) occurs which is analogous to the variation in the distance between the upper 180 and lower 181 surfaces of a conventional ridge-groove bearing of FIG. 9A.

In the first term of (3), $h^3$ changes from $h_0^3$ to $(h_0+h_g)^3 > h_0^3$, and back. In the second term of (3), h changes from h to $(h_0+h_g) > h_0$ and back.

Therefore, it can clearly be seen that an arrangement of "slip" and "no-slip" regions provided on a bearing surface in an interleaved pattern will have a similar effect on the lubricant as a pattern of ridges and grooves. The relative movement of such a pattern in a lubricant will cause pumping action to be induced in the lubricant.

This theory can be extended. For example, a herringbone pattern of "slip" and "no-slip" regions on the surface of a radial bearing has substantially the same effect as a herringbone pattern of ridges and grooves. A spiral pattern of "slip" and "no-slip" regions on the surface of an axial bearing will have substantially the same effect as a spiral pattern of ridges and grooves.

The same reasoning can be applied to an interleaved pattern of "high-slip" and "low-slip" regions. In other words, the high-slip region is chosen as $\alpha_1$, and the low-slip region is chosen as $\alpha_2$. In embodiments of the invention, there is a substantial difference between these values. For these conditions, a variation in the terms of (3) occurs between:

$$h^3\left[1 + \frac{3\alpha_1\mu}{h + \alpha_1\mu}\right] \text{ to } h^3\left[1 + \frac{3\alpha_2\mu}{h + \alpha_2\mu}\right] > h^3\left[1 + \frac{3\alpha_1\mu}{h + \alpha_1\mu}\right] \quad (7)$$

And between:

$$h\left[1 + \frac{\alpha_1\mu}{h + \alpha_1\mu}\right] \text{ to } h\left[1 + \frac{\alpha_2\mu}{h + \alpha_2\mu}\right] > h\left[1 + \frac{\alpha_1\mu}{h + \alpha_1\mu}\right] \quad (8)$$

Although this development has been made in terms of one interleaved region, or regions with different fluid slip characteristics, it will be appreciated by the person skilled in the art that if the upper bearing surface 184 was also coated with interleaved regions having different fluid slip characteristics, a similar effect would be induced in the lubricant portions in contact with the upper bearing surface according to the previous discussion.

Therefore, it has been shown that a hydrodynamic bearing can be provided by providing a bearing wherein primary and/or secondary bearing surfaces comprise first regions having a first fluid slip characteristic, and second regions having a second fluid slip characteristic substantially different to that of the first fluid slip characteristic. The second and first regions are disposed in an interleaved pattern over the primary and/or secondary bearing surfaces. Relative movement between the primary and secondary bearing surfaces induces a pumping action in the body of a lubricant in contact with the primary and/or secondary bearing surfaces, wherein the pumping action is induced by the difference in fluid slip characteristics between portions of lubricant in contact with the interleaved pattern of the first and second materials.

The equations derived above can be applied in relation to the design of a hydrodynamic bearing using a computational fluid dynamics solver (finite element solver), such as "Ansys", or using custom written software. Many different patterns of interleaved materials which will result in a pumping action may be designed using the above analysis.

Figure 10:
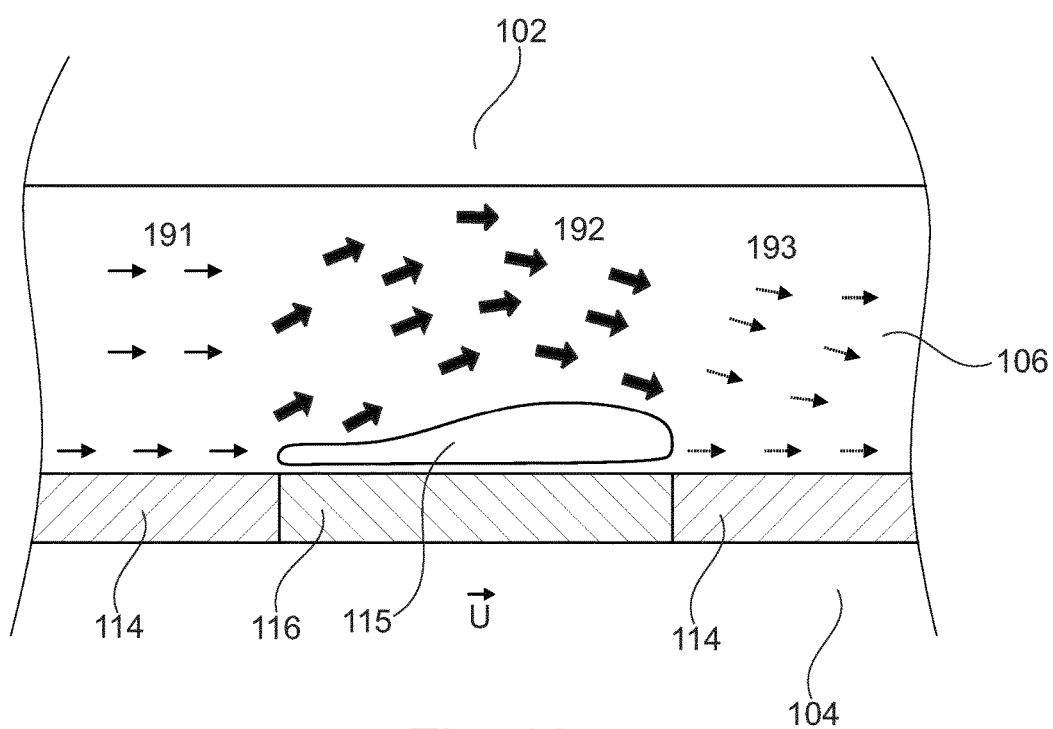
FIG. 10 shows an exemplary interleaved pattern in contact with a fluid.

FIG. 10 illustrates the effect of the first 114 and second 116 interleaved regions having first and second fluid slip characteristics which are substantially different to each other. The bearing bushing 102 and bearing shaft 104 enclose a bearing gap containing lubricant 106. Relative movement $\vec{U}$ between the bearing surfaces occurs. In this illustration, regions 114 are regions having slip. Regions 116 are regions having no slip. At region 191, the pressure p in the lubricant is relatively low, as denoted by the small arrows, and the surface of the first region 114, boundary layer between the first region and the lubricant 106, and the lubricant all move at different velocities.

In contrast, at region 192, the second region 116 is a "non-slip" material. The implication of this is that the surface of the second region 116, and the boundary layer of the lubricant 106 in contact with the second region 116 both move with velocity $\vec{U}$. This presents an obstacle to fluid moving from an area with "slip". This slow moving area of fluid is denoted with the contour 195. The deviation of the lubricant around this slow moving region increases the pressure p in the remainder of the lubricant 106, denoted by the larger vector arrows at 192. Once moving over a region coated with a slip material, the pressure p drops again, as at region 193. In this way, a pumping action is generated in the lubricant 106.

According to the invention, there is provided an X-ray tube 200. The X-ray tube comprises a rotating anode 202, a cathode 204 and a hydrodynamic bearing 206 as previously described. The rotating anode is supported on the rotatable bushing of the hydrodynamic bearing, and the anode disc provides a rotatable surface which is configured to generate X-rays as a result of electrons, emitted by the cathode, impinging on the rotatable disc.

Figure 11:
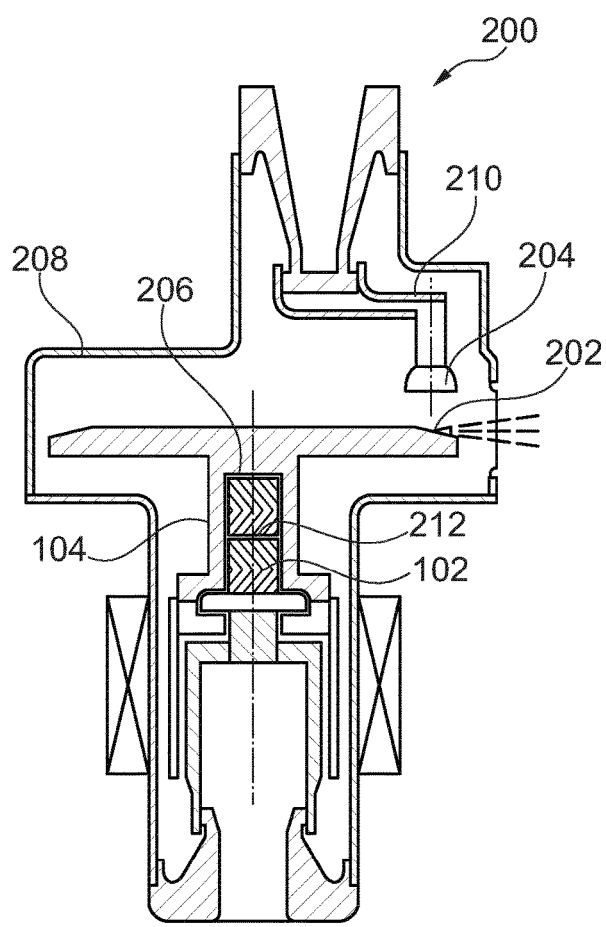
FIG. 11 shows an example of an X-ray tube.

FIG. 11 provides an illustration of an X-ray tube according to the invention. The X-ray tube 200 comprises a metal frame 208 to which the cathode 204 is connected via a cathode isolator 210. The anode comprises an anode disk 202 and is designed as a rotatable-anode. The anode is connected to the metal frame 208 via an anode isolator. The cathode 204 is adapted for emitting electrons towards the anode disk 202, while the anode disk 202 provides a rotatable surface which generates X-rays as a result of electrons emitted by the cathode 204 impinging on the anode disk. The X-rays leave the metal frame 208 via an X-ray window, for example, made of beryllium. The rotatable anode disk is supported by the hydrodynamic bearing 206 and is connected to the anode isolator. The bearing shaft 102 is connected to a support and is concentrically enclosed by the bearing bushing 104. Furthermore, the bearing bushing is connected to a rotor such that the anode disk rotates when power is provided to the X-ray tube.

The bearing shaft comprises a bore, parallel to the longitudinal axis of the hydrodynamic bearing, within which a cooling fluid or lubricant circulates. Alternatively, the anode disk is connected to the rotatable shaft, and the bearing is stationary.

The bearing shaft 102 is provided with an interleaved pattern of first and second regions 212, wherein the first region comprises a material having a first fluid slip characteristic, and the second region comprises a second material comprising a second fluid slip characteristic, wherein the fluid slip characteristics of the first and second regions are substantially different.

The bearing gap between the shaft and the bearing bushing is filled with a metal eutectic material acting as a lubricant. During the rotation of the anode in a prescribed direction of rotation, the interleaved pattern in the bearing acts on the lubricant as a pump to maintain the metal eutectic inside the bearing gap. The metal eutectic (lubricant) transfers forces acting radially or axially to the hydrodynamic bearing.

As previously discussed, the X-ray tube comprises a bearing arrangement with a primary bearing surface 110 disposed on the bearing bushing arranged to face a secondary bearing surface 112 disposed on the bearing shaft.

Therefore, in an X-ray tube comprising a hydrodynamic bearing according to the invention, a bearing can be provided which performs the hydrodynamic bearing pumping functions with a reduced, or zero, number of grooves. Advantageously, this leads to more efficient bearing operation because substantially zero shear stress is exerted on surfaces of the bearing. In addition, the bearing components are easier to manufacture because grooves which must be etched using complicated processes are reduced or removed.

According to the invention, an X-ray imaging system 250 is provided comprising an X-ray tube 200 as previously described, an X-ray detector 252, a support 254 for receiving an object 256, and a processing device 258.

Figure 12:
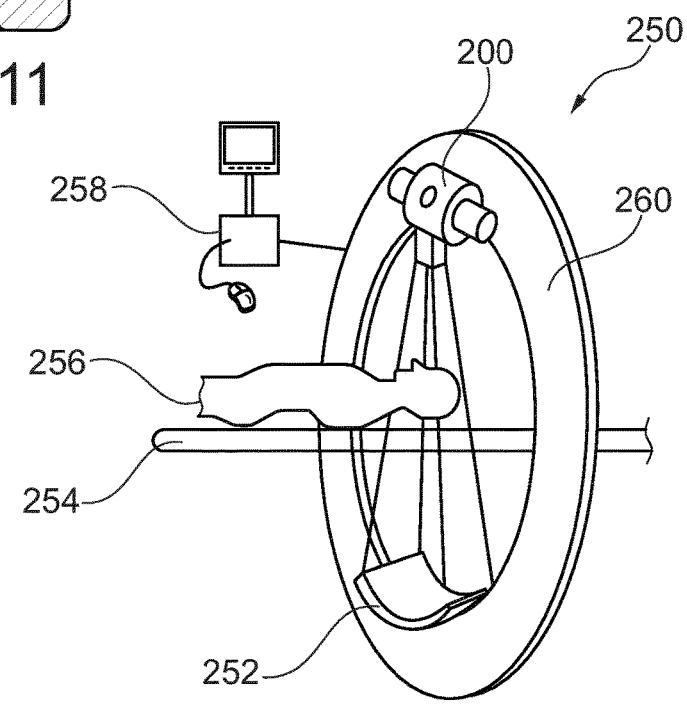
FIG. 12 shows an example of an X-ray system.

FIG. 12 illustrates an X-ray imaging system according to the invention. In FIG. 12, the X-ray imaging system is implemented as a CT system, although the X-ray imaging system can be provided as a C-arm system, or a luggage scanner.

The X-ray imaging system according to the invention comprises an X-ray tube 200 incorporating a hydrodynamic bearing as previously described, and an X-ray detector 252. The X-ray tube 200 and the X-ray detector 252 are arranged a gantry 260. The gantry 260 provides a rotational movement of the tube 200 and the detector 252 with respect to the object 256. The imaging system 250 further comprises a support 254 for receiving the object 256. The object 256 may, for example, be a patient. The X-ray tube 200 is adapted to generate X-ray radiation and the X-ray detector 252 is adapted to receive the X-ray radiation after the radiation passes through the object 256 on the support 254.

The processing device 258 is adapted to control the X-ray radiation by controlling the velocity of the rotor connected to the anode disk dependent on a load voltage acting on the hydrodynamic bearing in the X-ray source.

According to an embodiment of the invention, the X-ray imaging system comprises a display and an interface device connected to the processing device 258. The display serves as a source and information for controlling the X-ray imaging system 250, as well as for showing the image results acquired by the X-ray detector 252. In a further exemplary embodiment of the invention, the X-ray tube 200 and the X-ray detector 252 is arranged on opposing ends of a C-arm. A C-arm enables different trajectories of the X-ray tube 200 and the X-ray detector 252 around the object 256 besides rotational movement.

According to the invention, a hard drive 300 is provided comprising a supporting member 302, a hard disk 304 comprising a central hub 306, a hydrodynamic bearing 308 according to the previous description, wherein the central hub of the hard disk is rotatably supported on the supporting member by the hydrodynamic bearing.

Figure 13:
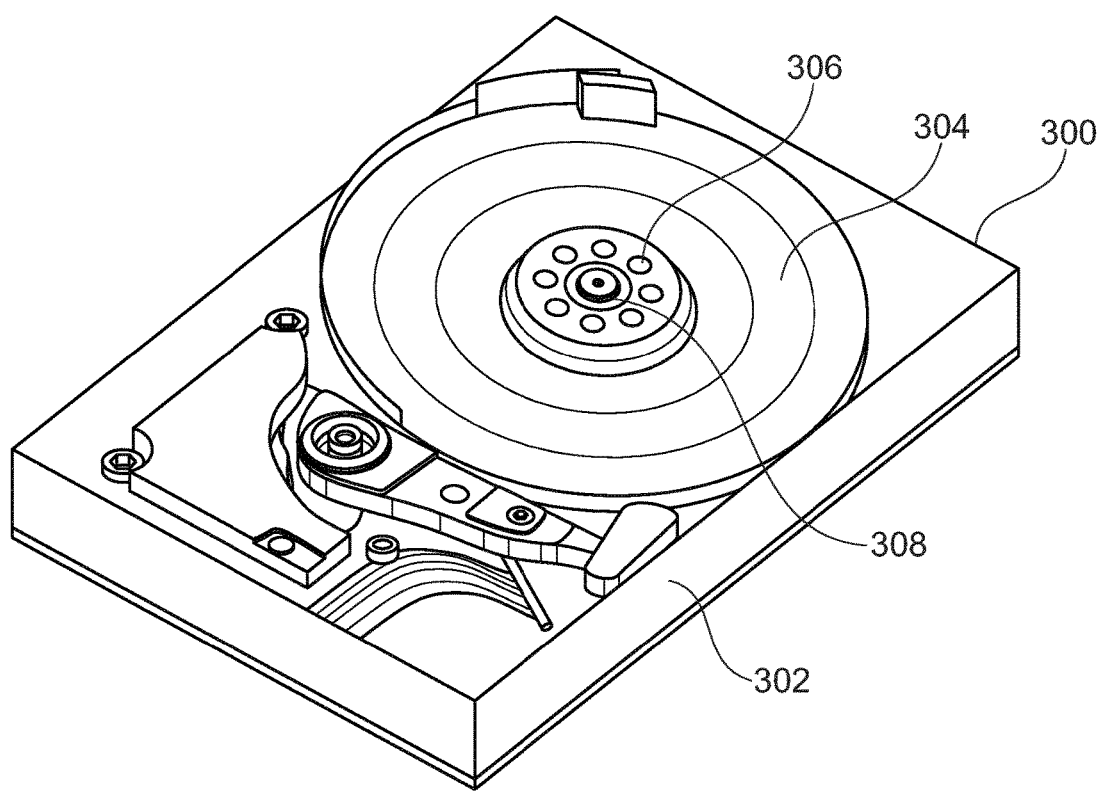
FIG. 13 shows an example of a hard drive.

FIG. 13 shows a computer hard drive according to the invention. A hard drive is another item requiring a bearing which must perform in demanding conditions. The principle outlined previously in relation to the hydrodynamic bearing for an X-ray tube can also be applied in a bearing for a hard drive. In this application, the temperature requirements are less demanding, but the speed and stability requirements are more demanding. For example, it is common for hard drives to rotate at 10,000 revolutions per minute.

In this case, the lubricant is a hydrocarbon derivative such as an oil, or an ester oil. Alternatively, the oil is silicone oil. The bearing parts are made from lower cost materials, such as phosphor bronze, or aluminium.

According to the invention, a method for manufacturing a hydrodynamic bearing is provided. The method comprises the steps of (a) providing 402 untreated bearing shaft and untreated bushing parts;

(b) forming 404 on the surface of the untreated bearing shaft and the untreated bushing parts a first region having a first fluid slip characteristic and a second region having a second fluid slip characteristic substantially different to that of the first fluid slip characteristic; wherein the second and first regions are disposed in an interleaved pattern over the one or more bearing surfaces;

wherein the first and second regions are formed by a coating of a material using plasma vapour deposition or chemical vapor deposition;

(c) assembling 406 the bearing shaft and bushing parts into a hydrodynamic bearing;

(d) adding 408 a lubrication material into a gap between the bearing shaft and the bushing;

(e) sealing 410 the bearing.

Figure 14:
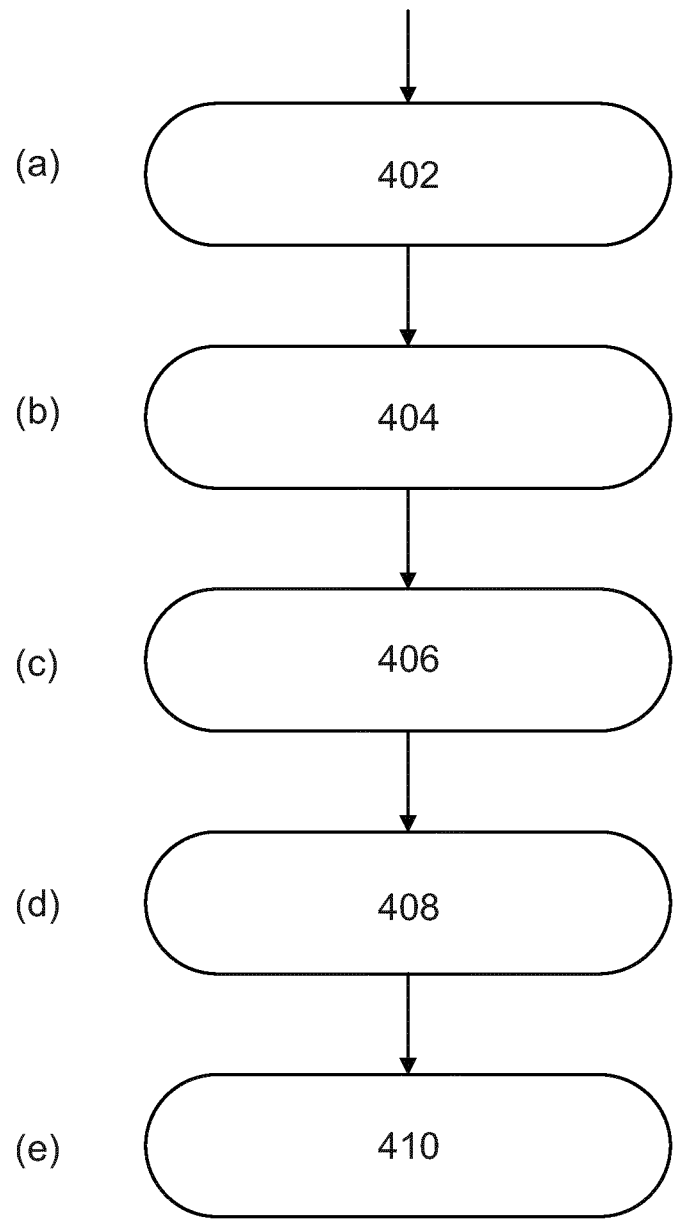
FIG. 14 shows an example of a method of manufacturing.

FIG. 14 illustrates the method according to the invention. Therefore, a hydrodynamic bearing can be manufactured in a simpler way, because a smaller proportion, or none, of the bearing will need to comprise grooves in the bearing surfaces. Such grooves are difficult to manufacture, requiring a laser ablation step or a chemical etching step. In comparison, in the present invention, first and second regions are disposed in an interleaved pattern over the one or more bearing surfaces. Such regions can be provided by a coating of a material formed by deposition.

According to an embodiment of the invention, a method is provided wherein in the step of forming on the surface of the untreated bearing shaft and the untreated bushing parts a first region having a first fluid slip characteristic and a second region having a second fluid slip characteristic, the formation of the first and/or second regions comprises depositing materials having a substantially planar characteristic using physical vapour deposition, plasma vapour deposition or chemical vapour deposition.

As is known to the skilled person, physical vapour deposition, plasma vapour deposition and chemical vapour deposition are coating deposition methods which are applied to a wide range of materials suitable for the present invention.

According to another embodiment of the invention, a method for manufacturing a hydrodynamic bearing comprising the further step after the forming step 402 of pre-treating either the bearing shaft, the bearing bushing, or both to improve their compatibility with the lubricant.

This step is appropriate when either the first or the second region is provided as a bare section of basis material, as described above. The pre-treatment is performed by heating in the presence of the lubricant and the basis material. Alternatively, the pre-treatment of the basis material region provided as the first or second region is performed by chemical treatment, by abrasive blasting, or by other methods known to those skilled in the art.

It should be noted that embodiments of the invention are described with reference to different subject-matters. In particular, some embodiments are described with reference to method type claims whereas other embodiments are described with reference to device type claims. A person skilled in the art will, however, gather from the above and following description that, unless other notified, in addition to any combination of features belonging to one type of the subject-matter, also any combination between features related to different subject-matter is considered to be disclosed with this application. All features can be combined providing synergetic effects that are more than simply a summation of the features.

While the invention has been illustrated and described in detail in the drawings and foregoing description, such illustration and description are to be considered illustrative or exemplary, and not restrictive. The invention is not limited to the disclosed embodiments. Other variations to the disclosed embodiments can be understood and effected by those skilled in the art practicing the claimed invention from a study of the drawings, the disclosure, and the dependent claims.

In the claims, the word "comprising" does not exclude other elements or steps and the indefinite article "a" or "an" does not exclude a plurality. A single processor or other units may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A self-acting, sealed hydrodynamic bearing, comprising:
   a bearing shaft;
   a bearing bushing arranged to seal a length of the bearing shaft;
   a lubricant provided in the sealed length of the hydrodynamic bearing; and
   a bearing arrangement provided between the bearing shaft and the bearing bushing;
   wherein at least one of the bearing shaft and the bearing bushing are configured to be rotatable;
   wherein the bearing arrangement comprises a primary bearing surface disposed on the bearing bushing, arranged to face a secondary bearing surface disposed on the bearing shaft,
   wherein at least one of the primary and secondary bearing surfaces comprise first regions having a first fluid slip characteristic, and second regions having a second fluid slip characteristic substantially different to that of the first fluid slip characteristic,
   wherein the first and second regions are in a same plane of a cross-section of the at least one of primary and secondary bearing surfaces to form a planar surface,
   wherein the second and first regions of the planar surface are disposed in an interleaved pattern over the at least one of primary and secondary bearing surfaces, and
   wherein relative movement between the primary and secondary bearing surfaces caused by a rotation of the at least one of bearing shaft and the bearing bushing induces a pumping action in a body of lubricant in contact with the primary and secondary bearing surfaces, wherein the pumping action is induced by the difference in the fluid slip characteristics between portions of lubricant in contact with the interleaved pattern of the first regions and the second regions.

2. The self-acting, sealed hydrodynamic bearing of claim 1, wherein the difference in the fluid slip characteristic between the first region and the second region is at least approximately 25%.

3. The self-acting, sealed hydrodynamic bearing of claim 1, wherein the first region is formed from a substantially planar coating of a first material, and the second region is formed from a substantially planar coating of a second material.

4. The self-acting, sealed hydrodynamic bearing of claim 3, wherein the thickness of the first material forming the first region is less than five microns.

5. The self-acting, sealed hydrodynamic bearing of claim 4, wherein the at least one of first and second regions comprised on one or more of the bearing surfaces are arranged around the rotation axis of the hydrodynamic bearing in a spiral pattern, a herringbone pattern, or a curved pattern.

6. The self-acting, sealed hydrodynamic bearing of claim 5, wherein the at least one of first and second regions of the interleaved pattern are provided in at least one of first and second sections of the at least one of first and second bearing surfaces, wherein the at least one of first and second sections are divided by a separation region.

7. The self-acting, sealed hydrodynamic bearing of claim 1, wherein the first region is coated with an ultra-nano-crystalline diamond film.

8. The self-acting, sealed hydrodynamic bearing of claim 1, wherein the sealed length is a vacuum-sealed bearing gap.

9. The self-acting, sealed hydrodynamic bearing of claim 1, wherein the bearing bushing and the bearing shaft are configured as a one of a conical bearing and as a spherical bearing.

10. A hard-drive, comprising:
a supporting member;
a disk comprising a central hub;
a self-acting, sealed hydrodynamic bearing according to claim 1;
wherein the central hub of the disk is rotatably supported on the supporting member by the hydrodynamic bearing.

11. The self-acting, sealed hydrodynamic bearing of claim 1, wherein the first region comprises a coating of any material selected from the group of: molybdenum disulphide, amorphous carbon, tetrahedrally coordinated amorphous carbon, polycrystalline diamond, and tungsten disulphide.

12. An X-ray tube, comprising:
a rotating anode;
a cathode; and
a self-acting, sealed hydrodynamic bearing including:
a bearing shaft;
a bearing bushing arranged to seal a length of the bearing shaft;
a lubricant provided in the sealed length of the hydrodynamic bearing; and
a bearing arrangement provided between the bearing shaft and the bearing bushing;
wherein at least one of the bearing shaft and the bearing bushing are configured to be rotatable;
wherein the bearing arrangement comprises a primary bearing surface disposed on the bearing bushing, arranged to face a secondary bearing surface disposed on the bearing shaft,
wherein at least one of the primary and secondary bearing surfaces comprise first regions having a first fluid slip characteristic, and second regions having a second fluid slip characteristic substantially different to that of the first fluid slip characteristic,
wherein the first and second regions are in a same plane of a cross-section of the at least one of primary and secondary bearing surfaces to form a planar surface,
wherein the second and first regions of the planar surface are disposed in an interleaved pattern over the at least one of primary and secondary bearing surfaces, and
wherein relative movement between the primary and secondary bearing surfaces caused by a rotation of the at least one of bearing shaft and the bearing bushing induces a pumping action in a body of lubricant in contact with the primary and secondary bearing surfaces, wherein the pumping action is induced by the difference in the fluid slip characteristics between portions of lubricant in contact with the interleaved pattern of the first regions and the second regions,
wherein the rotating anode is supported on the bearing bushing of the hydrodynamic bearing, and
wherein the rotating anode provides a rotatable surface which is configured to generate X-rays as a result of electrons, emitted by the cathode, impinging on the rotatable anode.

13. An X-ray imaging system, comprising:
an X-ray tube according to claim 12;
an X-ray detector;
a support for receiving an object; and
a processing device.

14. A method for manufacturing a self-acting, sealed hydrodynamic bearing, comprising the acts of:
(a) providing untreated bearing shaft and untreated bushing parts;
(b) forming on a surface of at least one of the untreated bearing shaft and untreated bushing parts a first region having a first fluid slip characteristic and a second region having a second fluid slip characteristic substantially different to that of the first fluid slip characteristic;
wherein the first and second regions are in a same plane of a cross-section of the surface of the at least one the untreated bearing shaft and untreated bushing parts;
wherein the second and first regions are disposed in an interleaved pattern over the surface of the at least one of the untreated bearing shaft and untreated bushing parts;
wherein the first and second regions are formed by a coating of a material using plasma vapour deposition or chemical vapor deposition;
(c) assembling the bearing shaft and bushing parts into a hydrodynamic bearing;
(d) adding a lubrication material into a gap between the bearing shaft and the bushing; and
(e) sealing the bearing.

* * * * *